US008470526B2

(12) United States Patent
Bukrinsky et al.

(10) Patent No.: US 8,470,526 B2
(45) Date of Patent: Jun. 25, 2013

(54) METHOD OF SUPPRESSING HUMAN IMMUNODEFICIENCY VIRUS (HIV) REPLICATION IN A SUBJECT BY ADMINISTERING A LIVER X RECEPTOR (LXR) AGONIST

(75) Inventors: Michael Bukrinsky, Potomac, MD (US); Dmitri Sviridov, Melbourne (AU)

(73) Assignee: The George Washington University, Washington, DC (US)

( * ) Notice: Subject to any disclaimer, the term of this patent is extended or adjusted under 35 U.S.C. 154(b) by 1848 days.

(21) Appl. No.: 11/528,431

(22) Filed: Sep. 28, 2006

(65) Prior Publication Data

US 2011/0033446 A1 Feb. 10, 2011

Related U.S. Application Data

(60) Provisional application No. 60/734,272, filed on Nov. 8, 2005, provisional application No. 60/721,116, filed on Sep. 28, 2005.

(51) Int. Cl.
*C12Q 1/70* (2006.01)

(52) U.S. Cl.
USPC .......................................................... 435/5

(58) Field of Classification Search
None
See application file for complete search history.

(56) References Cited

PUBLICATIONS

Miedzinski, L. J., 1992, Early clinical signs and symptoms of HIV infection, Can. Fam. Phys. 38:1401-1410.*
Mujawar, Z., 2010, Mutation of the ATP cassette binding transporter (ABCA1) C-terminus disrupts HIV-1 Nef binding but does not block the Nef enhancement of ABCA1 protein degradation, Biochem. 49:8338-8349.*
Gait, M. J., and J. Karn, 1995, Progress in anti-HIV structure-based drug design, TIBTECH 13:430-438.*
Von Rompay, K. K. A., 2010, Evaluation of antiretrovirals in animal models of HIV infection, Antivir. Res. 85:159-175.*
Terasaka, N., et al., 2003, T-0901317, a synthetic liver X receptor ligand, inhibits development of atherosclerosis in LDL receptor-deficienc mice, FEBS Letters 536:6-11.*
Stein, J. H., 2003, Dyslipidemia in the era of HIV protease inhibitors, Prog. Cardiovasc. Dis. 45(4):293-304.*
Millatt, L. J., et al., 2003, Liver X receptors and the control of cholesterol homeostasis: potential therapeutic targets for the treatment of atherosclerosis, Biochim. Biophys. Acta 1631:107-118.*
Lund, E. G., et al., 2003, Liver X receptor agonists as potential therapeutic agents for dyslipidemia and atherosclerosis, Arterioscler. Thromb. Vasc. Biol. 23:1169-1177.*
Geyeregger, R., et al., 2006, Liver X receptors in cardiovascular and metabolic disease, Cell. Mol. Life Sci. 63:524-539.*
Fievet, C., and B. Staels, 2009, Liver X receptor modulators: effects on lipid metabolism and potential use in the treatment of atherosclerosis, Biochem. Pharmacol. 77:1316-1327.*
Miedzinsky et al, Early clinical signs and symptoms of HIV infection; Canadian Family Physician, vol. 38, 1401-1410(1992).
Mickael J. Gait et al, Progress in anti-HIV structure-based drug design, Tibtech Reviews, vol. 13, 430-437(1995).
Ekoen et al, volution of anitvirals in animal models of HIV infection, Antiviral Research,vol. 85, 159-166 (2010).
Ekoen et al, volution of anitvirals in animal models of HIV infection, Antiviral Research,vol. 85, 166-175(2010).
Zahedi Mujawar et al, Mutation of the ATP cassette binding transporter A1 (ABCA1) C-terminus distrupts HIV-1 Nef binding, Biochemistry, vol. 49, 8338-8349 (2010).
Matthew P Morrow et al, Stimulation of Liver X receptor pathway inhibits HIV-1 replication, Mol. Pharmacol. vol. 78, 215-225 (2010).
T Neumann et al, Cardiovascular risk factors and probability for cardiovascular events in HIV infected patients, Eur. J. Med. Res. vol. 8, 229-235 (2003).
JC Maziere, Lovastatin inhibits HIV expression in H9 human T lymphocytes cultured in cholestrol poor medium, Biomed & Pharmacother, vol. 48, 63-67(1994).
Ono A, Freed EO (2001) Plasma Membrane Rafts Play a Critical Role in HIV-1 Assembly and Release. Proc Natl Acad Sci U S A 98: 13925-13930.

* cited by examiner

*Primary Examiner* — Jeffrey S. Parkin
(74) *Attorney, Agent, or Firm* — Houri Khalilian; Law Offices of Khalilian Sira, LLC

(57) ABSTRACT

The present invention provides novel methods for treating and preventing coronary artery disease in HIV-1-infected individuals by interfering with Nef-mediated effect on ABCA1. The invention further provides novel methods for suppressing HIV infection by stimulating cholesterol efflux from cells by stimulating expression of ABCA1 in HIV-1-infected individuals. These methods take advantage of the finding that Nef, a regulatory protein of HIV-1, (1) diminishes expression of ATP-binding cassette transporter A1 (ABCA1), the main transporter of cholesterol from cells to extracellular acceptors; and (2) impairs cholesterol efflux from HIV-1-infected macrophages leading to cholesterol accumulation and formation of foam cells, which is a characteristic feature of atherosclerosis.

5 Claims, 9 Drawing Sheets

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: PCR Primer

<400> SEQUENCE: 1
gagcctcccc aggagtcg                                                  18

<210> SEQ ID NO 2
<211> LENGTH: 25
<212> TYPE: DNA
<213> ORGANISM: Artificial Sequence
<220> FEATURE:
<223> OTHER INFORMATION: PCR Primer

<400> SEQUENCE: 2
caaacatgtc agctgttact ggaag                                          25

<210> SEQ ID NO 3
<211> LENGTH: 20
<212> TYPE: DNA
<213> ORGANISM: Artificial Sequence
<220> FEATURE:
<223> OTHER INFORMATION: PCR Primer

<400> SEQUENCE: 3
gccgtaccac tggcatcgtg                                                20

<210> SEQ ID NO 4
<211> LENGTH: 17
<212> TYPE: DNA
<213> ORGANISM: Artificial Sequence
<220> FEATURE:
<223> OTHER INFORMATION: PCR Primer

<400> SEQUENCE: 4
gtggtggtga agctgta                                                   17
```

METHOD OF SUPPRESSING HUMAN IMMUNODEFICIENCY VIRUS (HIV) REPLICATION IN A SUBJECT BY ADMINISTERING A LIVER X RECEPTOR (LXR) AGONIST

PRIORITY

This application claims priority benefit under 119(e) to U.S. 60/734,272 filed Nov. 8, 2005, and to U.S. 60/721,116 filed Sep. 28, 2005.

GOVERNMENT INTEREST

The invention was made, in part, with Government support under (1) contract R03 TW 06238-01, awarded by the National Institutes of Health/Fogarty International Center; (2) contract #317810, awarded by the National Health and Medical Research Council of Australia. The U.S. and Australian government have certain rights in this invention.

BACKGROUND OF INVENTION

1. Field of the Invention

The present invention relates to the field of treating coronary artery disease in HIV-1-infected individuals by interfering with Nef-mediated effect on ABCA1. The invention further relates to suppressing HIV infection by stimulating cholesterol efflux from cells by stimulating expression of ABCA1 in HIV-1-infected individuals.

2. Discussion of Background Information

Cardiovascular disease is a leading cause of death and disability among most of the world's population. Atherosclerosis is the major cause of cardiovascular and cerebrovascular disease and it leads to insufficient blood supply to critical body organs resulting for example, in heart attack, stroke and kidney failure. People suffering from hypertension, diabetes, and HIV infection are at especially high risk of developing atherosclerosis.

While the pathogenesis of atherosclerosis is complex and not completely understood, an underlying pathology led to the numerous theories for the cause of atherosclerosis, for example, an increase in serum cholesterol and the accumulation of cholesterol esters in the arterial wall. Foam cells are the key elements of atherosclerotic plaque formation[1]. These cells form the cholesterol laden core of the plaque which later undergoes necrosis and calcification and can go on to rupture. The reason for accumulation of foam cells and cholesterol in the vessel wall may be dyslipidemia, especially high levels of low density lipoproteins (LDL) and low levels of high density lipoprotein (HDL), and/or impairment of intracellular cholesterol metabolism. Most likely, both mechanisms contribute to increased risk of CAD (coronary artery disease) in HIV-infected patients as HIV infection targets cholesterol metabolism in the cells central to the development of atherosclerosis, i.e., macrophages, while antiretroviral therapy causes dyslipidemia[2,3].

Cholesterol efflux is a pathway for removing excessive cholesterol from cells to extracellular acceptors. It plays a key role in maintaining cell cholesterol homeostasis. Impairment of cholesterol efflux leads to accumulation of intracellular cholesterol[4] and development of atherosclerosis in animal models[5] and in humans[6,7].

While previous studies demonstrated that cholesterol is essential for HIV-1 budding and infectivity[8-10] and that HIV-1 protein Nef can directly bind cholesterol and transport it to the site of HIV assembly at the plasma membrane[11], the significance of Nef in diminishing the expression of ATP binding cassette transporter A1 (ABCA1), the main transporter of cholesterol from cells to extracellular acceptors, and impairing cholesterol efflux, which leads to cholesterol accumulation and formation of foam cells, remains unknown. These previous studies make no mention of Nef as a cause of CAD in HIV-1-infected individuals. No effect of Nef on ABCA1 activity has been previously described. Further, negative relation between the level of ABCA1 expression in a particular cell and infectivity of HIV-1 produced by this cell has not been previously recognized.

The present invention provides these heretofore needed tools, as well as methods for treating CAD in HIV-infected patients by preventing Nef from binding to ABCA1 in HIV-1-infected cells or/and by stimulating expression of ABCA1 thereby simultaneously suppressing HIV replication.

A. Monocyte-derived macrophages were inoculated with indicated HIV-1 strains equalized according to RT activity and cultivated for 21 days (RT activity in the culture supernatants on day 21 is shown underneath the bars). Mock-infected cells were incubated with virus-free medium. Specific cholesterol efflux to apoA-I (30 μg/ml) was performed for 12 h and analyzed as described in Methods. Results are presented as percentage of efflux from mock-infected cells (taken as 100%) and are mean±SD of triplicate determinations. *$p<0.001$ B. Monocyte-derived macrophages were inoculated with VSV-G-pseudotyped HIV-1 SF2 either deficient in Nef (SF2.Nef) or carrying wild-type Nef (SF2.wt). Specific cholesterol efflux to apoA-I (30 μg/ml) was analyzed on day 6 after inoculation using the same procedure as described in panel A. p24 concentration in the culture medium is shown underneath the bars. Results are presented as percentage of efflux from mock-infected cells (taken as 100%) and are mean±SD of triplicate determinations. *$p<0.001$ C. RAW 264.7 cells were transfected with plasmids expressing indicated Nef variants or an empty vector (mock-transfection). Twenty four hours after transfection, LXR agonist, TO-901317 (1 μmol/L), was added. Cholesterol efflux to apoA-I (30 μg/ml) was performed for 3 h with cells 48 h after transfection as described in Methods. Means±SD of quadruplicate determinations are shown, *$p<0.001$.

D. Immunoblotting of RAW 264.7 cells transfected with empty vector (mock), wild-type Nef derived from HIV-1 strain SF2 (Nef.wt), or Nef.G2A mutant and stained with anti-Nef antibodies.

Figure 2:
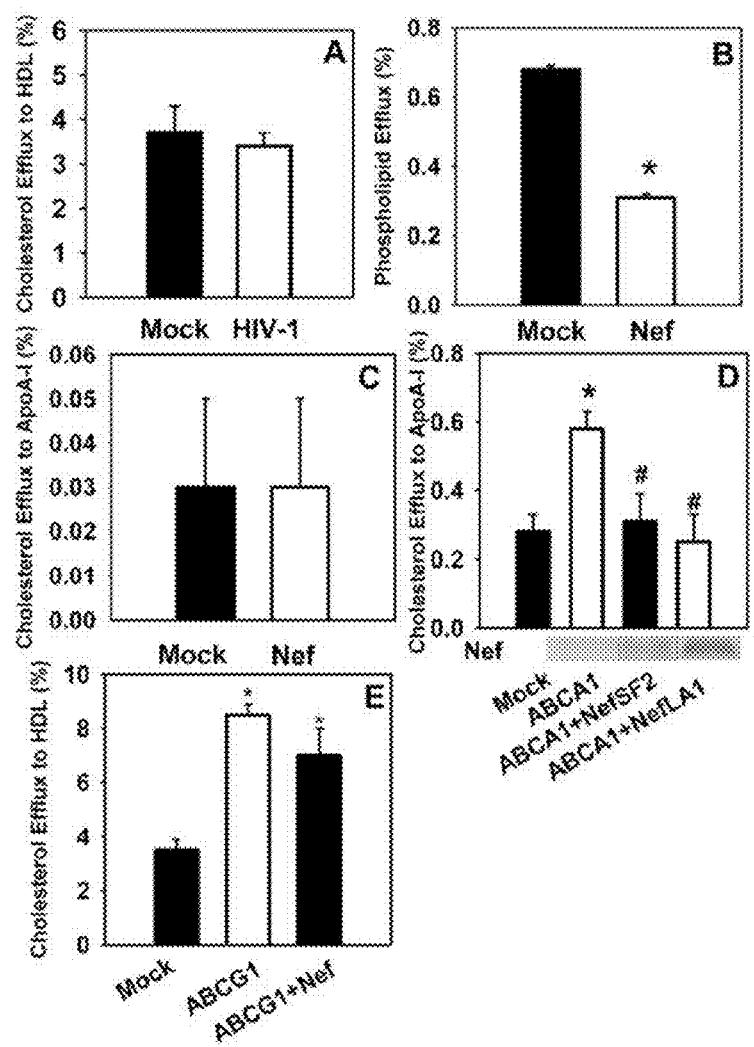

FIG. 2. Nef targets ABCA1-dependent cholesterol efflux

A—Cholesterol efflux to HDL (30 ug/ml) was measured from HIV-1 ADA-infected and mock-infected macrophages used also to measure efflux to apoA-I in FIG. 1A.

B—Impairment of phospholipid efflux in Nef-transfected RAW 264.7 cells. RAW 264.7 cells were transfected with plasmid expressing HIV-1 SF2-derived Nef or empty vector (mock-transfection). Phospholipid efflux to apoA-I (30 ug/ml) was measured as described in Methods. Means±SD of quadruplicate determinations are shown, *$p<0.001$.

C—Nef does not decrease cholesterol efflux in RAW 264.7 cells not treated with LXR agonist. Experiment was performed using HIV-1 SF2-derived Nef as described in FIG. 1C, except that LXR agonist was not added.

D—Cholesterol efflux to apoA-I from HeLa cells. HeLa cells were co-transfected with ABCA1 and empty vector (mock) or vector expressing Nef derived from HIV-1 SF2 (NefSF2) or LAI strains (NefLAI) and cholesterol efflux to apoA-I was analyzed. *p<0.001 (versus cells without ABCA1); #p<0.001 (versus cells without Nef). Expression of Nef determined by Western blot is shown underneath the bars.

E—Cholesterol efflux to HDL from HeLa cells. Experiment was performed as in panel D, except that ABCG1 was used instead of ABCA1, and HDL (30 µg/ml) instead of apoA-I was used as cholesterol acceptor. *p<0.01 (versus cells without ABCG1).

Figure 3:
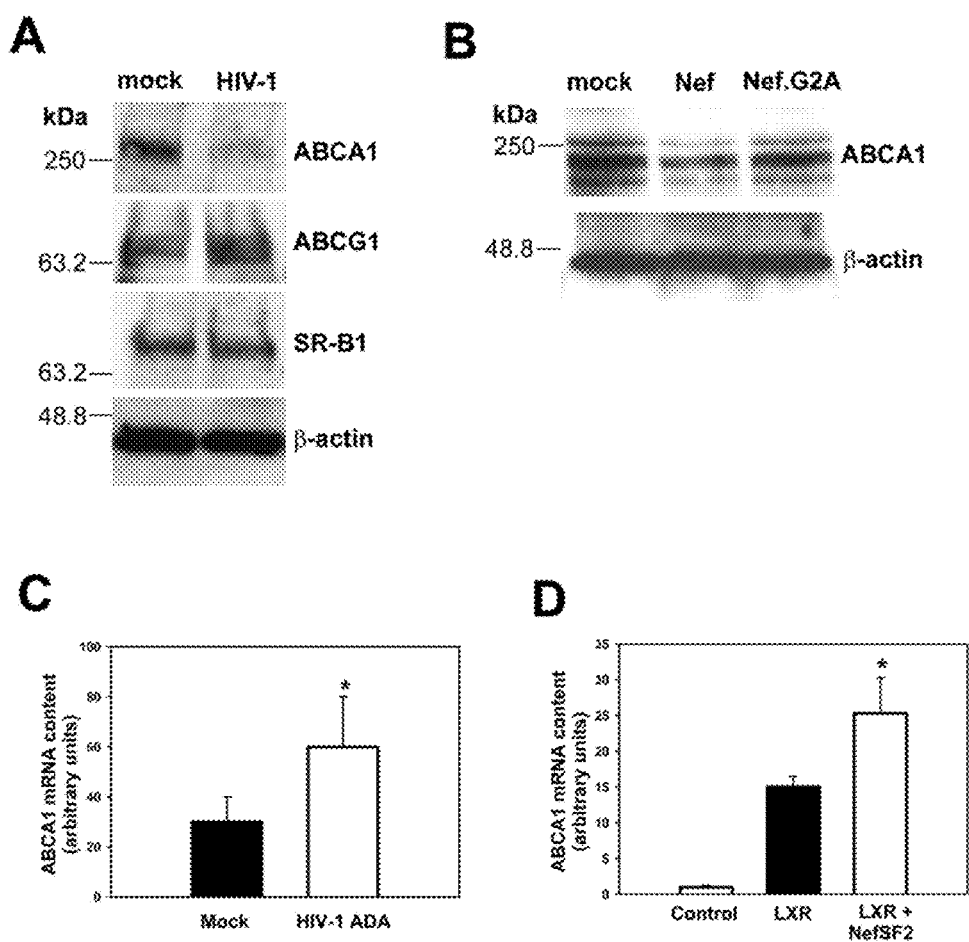

FIG. 3. Nef induces downmodulation of ABCA1

A—Human monocyte-derived macrophages were infected with HIV-1 ADA or mock-infected and cultured for 14 days (RT in culture supernatant was 4,000 cpm/µl). ABCA1, ABCG1, SR-B1 and B-actin (loading control) were analyzed by Western blotting.

B—RAW 264.7 cells were transfected with vector expressing HIV-1 SF2-derived Nef (either wild-type or carrying a G2A mutation) or empty vector (mock). Twenty four hours after transfection, cells were stimulated with TO-901317 (1 µM) and 24 h later were analyzed by Western blotting for ABCA1 and B-actin (loading control).

C—ABCA1 RNA from HIV-infected macrophages used for Western blotting in panel A was analyzed by real-time RT-PCR. Results were adjusted according to B-actin signal and are presented in arbitrary units; *p<0.01 (versus mock).

D—RNA was extracted from non-activated RAW 264.7 cells (control), mock-transfected RAW cells activated with LXR agonist TO-901317 (LXR), or cells transfected with SF2-derived Nef and activated with TO-901317 (LXR+ NefSF2), and analyzed by real-time RT-PCR. Results were adjusted according to 28S RNA signal and are presented in arbitrary units; *p<0.01 (versus LXR agonist-treated mock-transfected cells).

Figure 4:
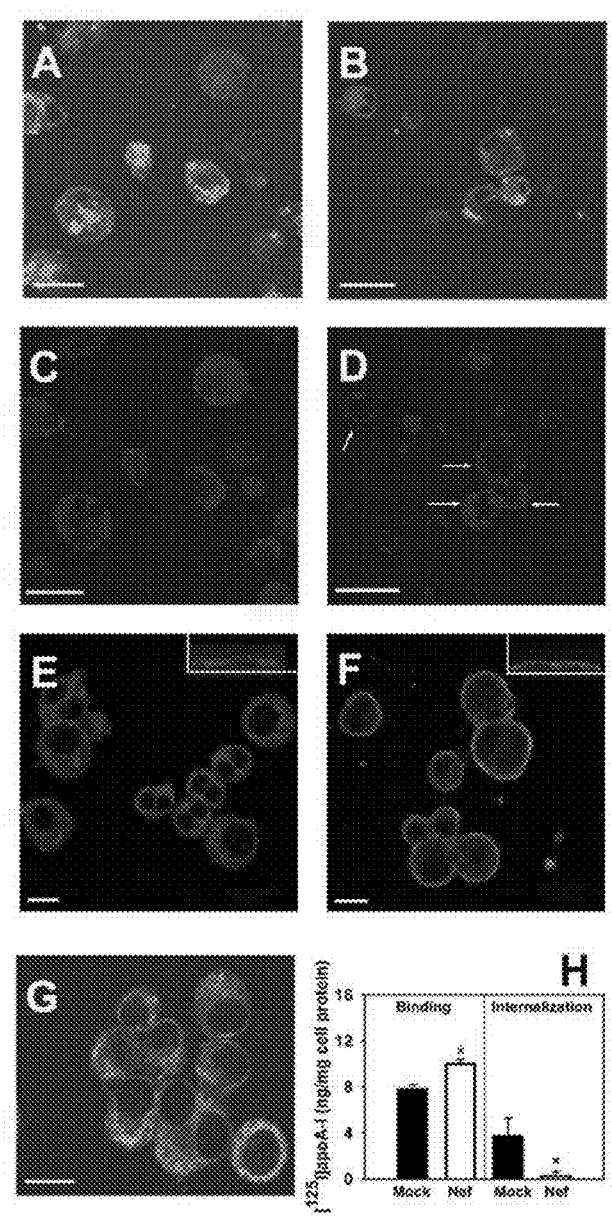

FIG. 4. The effect of Nef on ABCA1 localization

A,B,C,D—On day 5 after infection with VSV-G-pseudotyped Nef-expressing (panels B and D) or Nef-deficient (panels A and C) HIV-1 SF2, cells were co-stained with anti-p24 mouse monoclonal and anti-ABCA1 rabbit polyclonal antibodies, followed by rhodamine-conjugated anti-mouse (panels A and B) and Cy5-conjugated anti-rabbit IgG (panels C and D). Arrows point to cells with re-localized ABCA1. The scale bars are 20 µm.

E,F,G—Distribution of ABCA1 revealed by staining with monoclonal anti-ABCA1 antibody and FITC-conjugated anti-mouse IgG in RAW 264.7 cells transfected with empty vector (panel E), wild-type Nef derived from SF2 HIV-1 (Nef.wt, panel F), or SF2 Nef carrying a G2A mutation (Nef.G2A, panel G). Insets in panels E and F show cross-section of the image reconstituted from serial sectioning. Scale bars—20 um.

H—[$^{125}$-I]apoA-I binding (left panel) and internalization (right panel) in RAW 264.7 macrophages transfected with HIV-1 SF2-derived Nef. *p<0.01.

Figure 5:
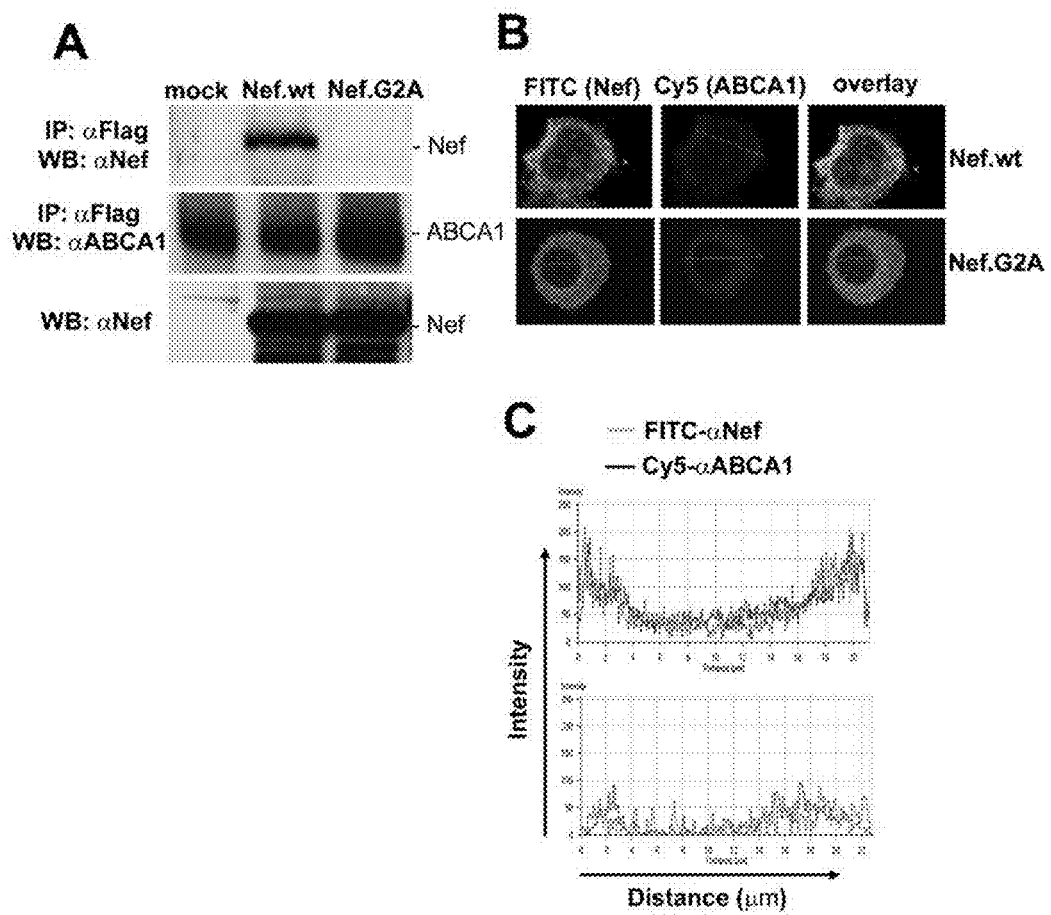

FIG. 5. Nef interacts with ABCA1

A. ABCA1 was immunoprecipitated using anti-FLAG M2 affinity gel from HeLa cells co-transfected with ABCA1-FLAG and an empty vector (mock), wild-type SF2 Nef (Nef.wt) or myristoylation-defective mutant Nef.G2A. Immunoprecipitates were analyzed by Western blotting for Nef (upper panel) or ABCA1 (middle panel) using specific antibodies. Bottom panel shows Nef expression in lysates of cells used for immunoprecipitation.

B. Experiment was performed as in FIG. 4E, except that cells were incubated with monoclonal anti-ABCA1 and polyclonal anti-Nef antibody, followed by FITC-conjugated anti-rabbit and Cy5-conjugated anti-mouse antibodies. Since all transfected cells show re-localization of ABCA1 (FIG. 4E), a typical single cell is shown here. Images were analyzed using software on the Zeiss LSM 510 microscope. The scale bar is 20 µm.

C. Fluorescence profile of the image in FIG. 5B was analyzed using the LSM 510 software. The top panel shows the distributions of the ABCA1 and HIV-1 Nef proteins in blue and green, respectively. The same analysis in the lower panel was performed for ABCA1 and Nef.G2A. The co-localization of wild-type Nef and ABCA1 at the plasma membrane is indicated by overlapping green and blue peaks at either end of the graph in the top panel.

Figure 6:
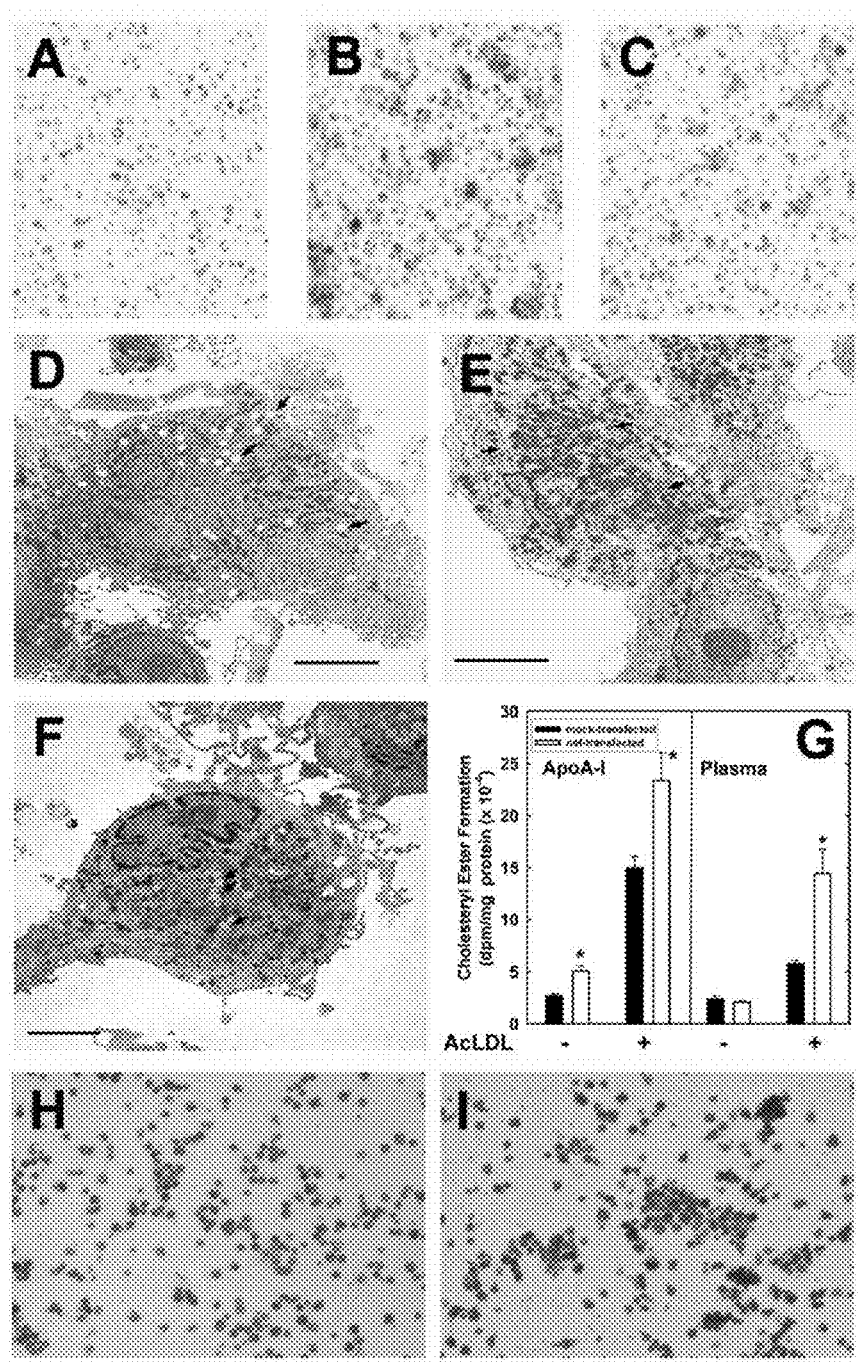

FIG. 6. Accumulation of lipids in cells infected with HIV-1 or transfected with Nef.

A,B,C.—Oil Red O staining of HIV-infected macrophages. Uninfected (A) macrophages or cells infected with VSV-G-pseudotyped Nef-positive (B) or Nef-deficient (C) HIV-1 SF2 variants were loaded with cholesterol on day 3 after infection by incubating with AcLDL in the presence of apoA-I and lipids were stained with Oil Red O 24 h later. p24 concentration in the culture supernatant on day 3 after infection was 4.7 ng/ml for cells inoculated with Nef-positive virus and 9.8 ng/ml for the culture inoculated with Nef-deficient HIV-1.

D,E,F—Electron microscopy of cholesterol loaded uninfected macrophages (D) and cells infected with Nef-positive (E) and Nef-deficient (F) HIV-1 AD8 performed 14 days after infection. Uninfected cells have small numbers of electron-lucent lipid vacuoles (arrows). The cytoplasm of cells infected with Nef-positive virus is filled with electron dense lipid vacuoles (arrows). Cells infected with Nef-deficient virus have small numbers of electron-lucent lipid vacuoles (arrows) similar in number to those in uninfected cells. The scale bars are 5 µm.

G—The effect of Nef on cholesteryl ester synthesis. The rate of cholesteryl ester synthesis in RAW 264.7 cells transfected with an empty vector (mock-transfected) or Nef-expressing construct and incubated with or without AcLDL in the presence of apoA-I or 5% human plasma is presented as mean±SD of quadruplicate determinations, *p<0.02.

H,I—RAW 264.7 cells were transfected with empty vector (H) or Nef-expressing construct (I), stimulated with LXR agonist, incubated with AcLDL and lipid-free apoA-I, fixed with formaldehyde and stained with Oil Red O.

Figure 7:
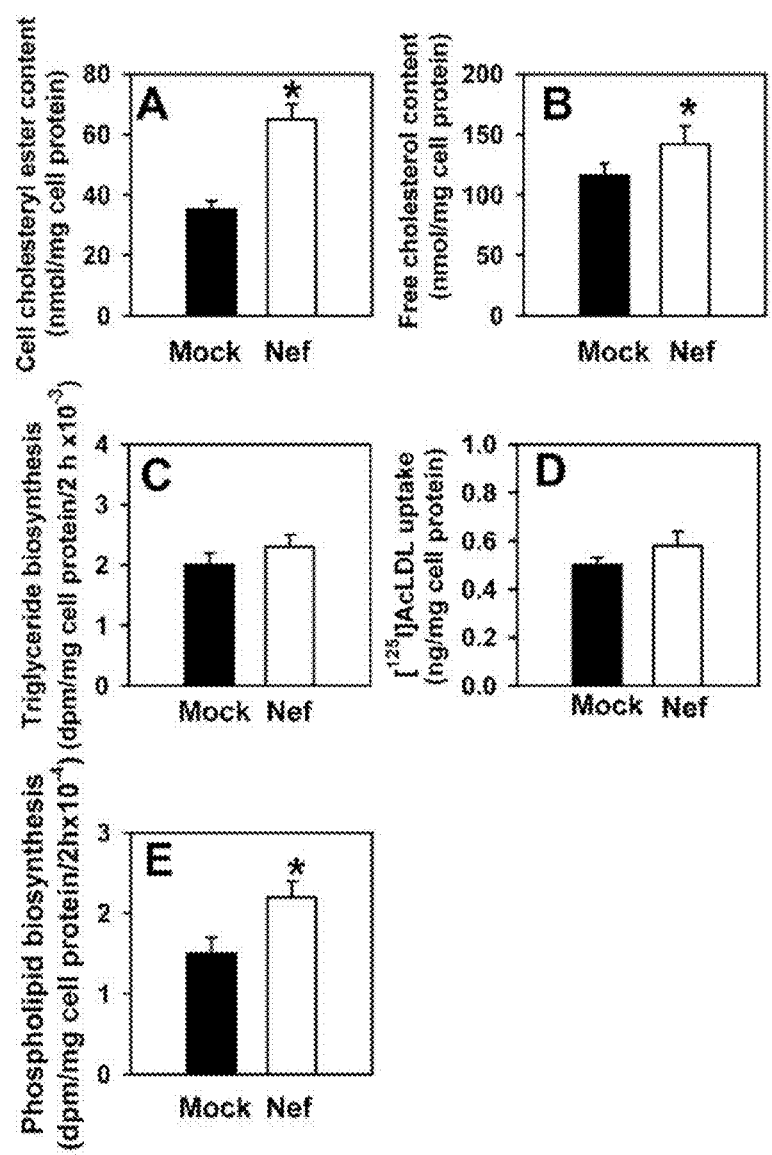

FIG. 7. Analysis of lipids in RAW 264.7 macrophages transfected with Nef.

A—Cholesteryl ester content after 24 h incubation with AcLDL (50 µg/ml) determined by enzymatic assay; *p<0.01.

B—Free cholesterol content after 24 h incubation with AcLDL (50 µg/ml) determined by enzymatic assay; *p<0.05.

C—Triglyceride biosynthesis after 24 h incubation with AcLDL (50 µg/ml) measured as incorporation of [$^{14}$C]oleic acid into triglycerides as described in Methods.

D—Uptake of AcLDL was calculated as a sum of $^{125}$I-AcLDL specifically taken up and degraded by cells.

E—Phospholipid biosynthesis measured as incorporation of [$^{14}$C]choline into phospholipid fraction as described in Methods; *p<0.01.

Figure 8:
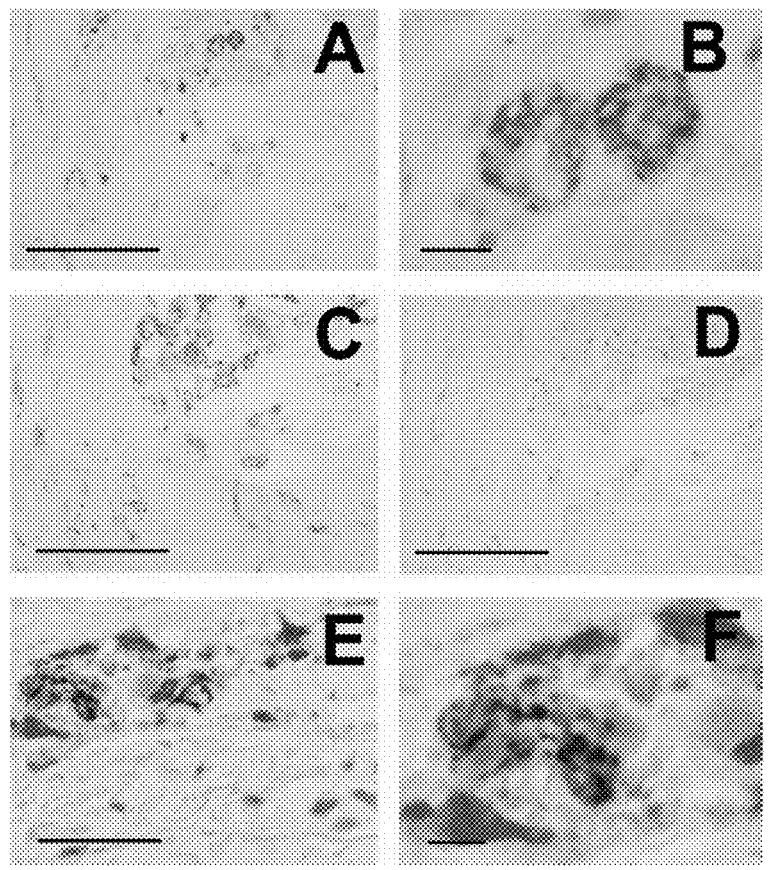

FIG. 8. Identification of HIV-1-positive macrophages in atherosclerotic plaques of HIV-infected subjects.

Single (panels A, B, C, D) and double (E, F) immunostaining of aortic wall segments.

A—p24 staining. A low magnification image showing the presence of p24$^+$ cells in an area adjacent to the plaque lipid core. The scale bar is 100 µm.

B—detail of panel A. p24$^+$ cells show a characteristic morphology of foam cells. The scale bar is 10 µm.

C—CD68 staining. CD68+ cells were identified in a parallel consecutive section to that shown in panel A. The scale bar is 100 µm.

D—negative control (staining with an irrelevant primary antibody). The scale bar is 100 µm.

E—double immunostaining showing the co-localization of p24 (brown) with CD68 (rose). Immunostaining included a combination of a rabbit polyclonal anti-p24 antibody in the peroxidase-anti-peroxidase system with DAB chromogen yielding a brown reaction product, and a mouse monoclonal antibody to CD68 in the alkaline phosphatase-anti-alkaline phosphatase system with Fast Red chromogen resulting in a rose precipitate. Counterstaining was with Mayer's haematoxylin. The scale bar is 50 µm.

F—a detail of panel E. The scale bar is 15 µm.

Figure 9:
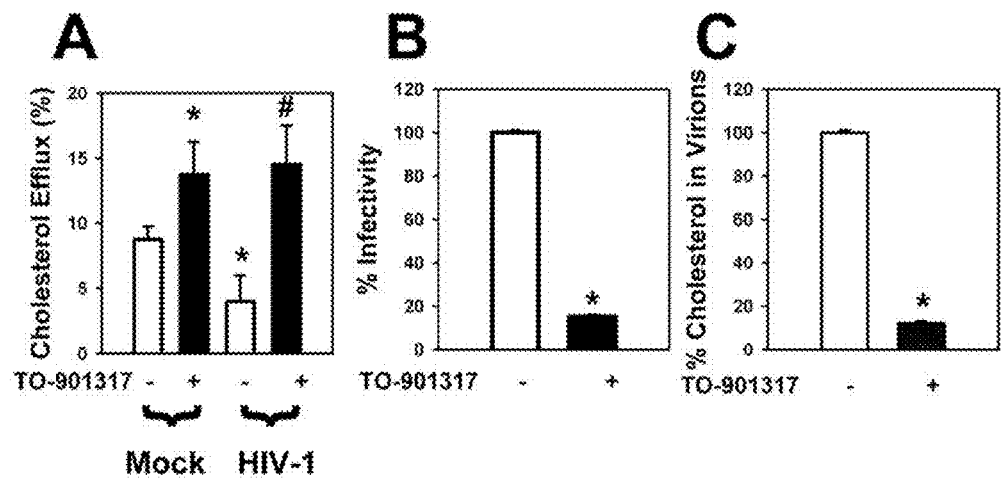

FIG. 9. Cholesterol efflux and infectivity of HIV virions

Human monocyte-derived macrophages were infected with HIV-1 ADA or mock-infected, and 7 days after infection were treated or not with LXR agonist, TO-901317 (500 nM), for 7 more days.

A—Cholesterol efflux to apoA-I was measured on day 21 after infection. *p<0.01 (versus uninfected cells not treated with TO-901317), *p<0.01 (versus HIV-infected cells not treated with TO-901317).

B—Virions were collected from culture supernatants of LXR agonist-treated and untreated (control) cells on day 10 and day 14 (pooled together), adjusted according to p24 content and analyzed for infectivity on indicator P4-CCR5 cells. Experiment was performed in triplicate and results (mean±SD) are presented as percent infectivity of virions produced by control cells; *p<0.001.

C—Incorporation of [$^3$H]cholesterol into virions produced by LXR agonist-treated and untreated (control) cells was measured in triplicate and results (mean±SD) are presented relative to cholesterol in the virions produced by control cells; *p<0.001.

SUMMARY OF THE INVENTION

The present invention relates to the identification of Nef as the causative factor for impairment of cholesterol efflux in HIV-1-infected cells. This discovery solves the problem related to unknown cause of high risk for coronary artery disease (CAD) in HIV-infected individuals. This discovery also identifies ABCA1 as a novel anti-HIV factor which suppresses infectivity of HIV. Cholesterol efflux from HIV-infected macrophages may be increased by stimulation of ABCA1 expression using for example chemical agonists of LXR/RXR or PPAR nuclear receptors. Such stimulation of ABCA1 expression and cholesterol efflux also inhibits HIV-1 replication and decreases infectivity of the virus. Thus, CAD in HIV-1 infected individuals can be treated by stimulating ABCA1 or by interfering with Nef-mediated effect on ABCA1. These treatments may include agonists of LXR/RXR and PPAR nuclear receptors. Nef-neutralizing intracellular antibodies or small molecules that prevent Nef binding to ABCA1. Further, HIV infection can be suppressed by stimulating cholesterol efflux from cells. By inhibiting Nef binding to ABCA1, ABCA1 is protected and is able to perform its efflux job; by using agonists to stimulate expression of ABCA1, ABCA1 is able to abundantly produce and bind all available Nef depriving virus of the necessary factor in addition to depriving it of cholesterol.

In preferred embodiments, there is provided the following methods.

A method of treating coronary artery disease in HIV-1 infected individuals comprising intracellular administering an effective amount of Nef-neutralizing antibody or a fragment thereof sufficient to inhibit the binding of Nef binding to ABCA1.

A method of treating coronary artery disease in HIV-1 infected individuals comprising intracellular administering an effective amount of Nef-targeting small molecules sufficient to inhibit the binding of Nef to ABCA1.

The method wherein said Nef-neutralizing antibody is a human polyclonal antibody, monoclonal antibody or a chimeric antibody.

A method of treating coronary artery disease in HIV-1 infected individuals comprising administering an effective amount of chemical agonist sufficient to stimulate expression of ABCA1 and cholesterol efflux from HIV-1 infected cells.

The method wherein the chemical agonist is an agonist of LXR, RXR or PPAR nuclear receptors.

A method of treating HIV-1 infection comprising administering an effective amount of chemical agonist sufficient to stimulate expression of ABCA1 in HIV-1 infected cells., wherein the chemical agonist is an agonist of LXR/RXR or PPAR nuclear receptors.

DETAILED DESCRIPTION OF THE INVENTION

HIV-1 infection, both treated and untreated, is associated with profound changes in lipid and lipoprotein metabolism[12,13] and increased risk of coronary artery disease (CAD)[14,17]. The major cause of CAD is atherosclerosis. The accumulation of cholesterol-loaded 'foam cells' (macrophages and possibly smooth muscle cells) in the walls of arteries is a characteristic feature of atherosclerosis. In this application, the inventor of the present invention demonstrates that HIV-1 infection of macrophages leads to impairment of apolipoprotein A-I (apoA-I)-dependent cholesterol efflux, accumulation of cholesterol and formation of foam cells. This effect is mediated by the HIV-1 protein Nef. Indeed, Nef-deficient HIV-1 does not impair cholesterol efflux, while transfection of murine macrophages with the Nef-expressing plasmid results in reduction of efflux and cholesterol accumulation. In cells infected with Nef-positive, but not with Nef-deficient HIV-1, as well as in cells transfected with Nef-expressing plasmid, the ATP-binding cassette transporter A1 (ABCA1), the main transporter of cholesterol to apoA-I, re-localized from the cytoplasm to the plasma membrane, showing that Nef-mediated re-distribution of ABCA1 is a mechanism responsible for impairment of cholesterol efflux. The role of HIV-infected macrophages in atherosclerosis is supported by the presence of HIV-positive foam cells in atherosclerotic plaques of HIV-infected patients. These results demonstrate a mechanism by which HIV-infected macrophages may contribute to atherosclerotic plaque formation.

In accordance with the present invention, Nef, a regulatory protein of HIV-1, diminishes activity and expression in HIV-infected macrophages of ATP binding cassette transporter A1 (ABCA1), the main transporter of cholesterol from cells to extracellular receptors, and impairs cholesterol efflux thus leading to cholesterol accumulation and formation of foam cells.

Discussion

Results presented in this report demonstrate that HIV-1, via the accessory protein Nef, impairs cholesterol efflux from macrophages. This finding can be interpreted as a virus-mediated switch of cholesterol trafficking from physiological efflux to virus-controlled transport, thus reducing the ability of a cell to export excessive cholesterol. Given that availability of cholesterol is critical for HIV assembly and infectivity

[48], it is physiologically sensible for the virus to take over control of intracellular cholesterol metabolism.

A previous report demonstrated that Nef binds cholesterol and may deliver it to nascent virions [5]. Our study suggests that Nef-mediated impairment of cholesterol efflux is another mechanism ensuring efficient delivery of cholesterol to HIV. Importantly, this mechanism may be a necessary component of the above-mentioned Nef-mediated transport of cholesterol to virions. Indeed, prevention of cholesterol efflux impairment by LXR agonist reduces virion-associated cholesterol without interfering with Nef incorporation into the virions (data not shown). Reduction of virion-associated cholesterol correlates with lower virion infectivity (FIGS. 9B,C).

Our results demonstrate that Nef specifically targets ABCA1. Indeed, Nef did not suppress cholesterol efflux in cells lacking ABCA1 (HeLa cells or non-activated RAW 264.7 cells), but did so in ABCA1-expressing cells, such as RAW 264.7 cells stimulated with an LXR agonist, HeLa cells transfected with ABCA1, and differentiated human macrophages. Furthermore, Nef did not suppress cholesterol efflux from ABCG1-transfected HeLa cells (FIG. 2E). These findings and the fact that Nef can interact with ABCA1 (FIG. 5A) suggest that there is an interplay between Nef and ABCA1 in an HIV-infected cell. The end result of this interplay would depend on relative levels of expression of Nef and ABCA1. Consistent with this suggestion, overexpression of Nef from the CMV promoter inhibits ABCA1-mediated cholesterol efflux stimulated with the LXR agonist (FIG. 1C), whereas levels of Nef expressed from the HIV LTR are insufficient to suppress LXR agonist-stimulated cholesterol efflux in HIV-infected macrophages (FIG. 9A). As a result, HIV infectivity is reduced in LXR agonist-stimulated cells (FIG. 9B). Therefore, drugs stimulating cholesterol efflux may provide a dual benefit to HIV-infected patients by limiting HIV replication and reducing the risk of atherosclerosis.

Our studies show that cholesterol efflux impairment is a conserved feature of HIV-1 Nef. Indeed, we show this phenomenon using 3 R5 (ADA, Yu-2 and 92US660) and 2×4 (SF2 and LAI) HIV-1 isolates. We demonstrate that HIV-1 Nef impairs cholesterol efflux by at least two mechanisms: it reduces ABCA1 abundance and causes intracellular re-distribution of ABCA1. These two mechanisms may be related, as they both depend on interaction between Nef and ABCA1 (FIGS. 3-5). For example, a block to intracellular trafficking of ABCA1 may re-target this protein to a degradation pathway. Alternatively, ABCA1 re-distribution and down-regulation may be two independent effects of Nef, both contributing to impairment of cholesterol efflux. Indeed, several recent reports demonstrated a role of ABCA1 trafficking between late endosomes and the cell surface in cholesterol efflux from endosomal compartment [36,38,39,49]. The effects of Nef on ABCA1 distribution and apoA-I binding and internalization are similar to the effects of cyclosporin A [43] or deletion of the PEST sequence in ABCA1 [39], both of which inhibit efflux of cholesterol from late endosomes. Therefore, both down-regulation of ABCA1 and its intracellular re-distribution can independently contribute to cholesterol efflux impairment observed in HIV-infected cells. Interestingly, Nef alone had less effect on ABCA1 abundance than HIV-1 infection (compare FIGS. 3A and 3B), however, it had a more profound effect on the sequestration of ABCA1 at the plasma membrane (compare FIGS. 4D and 4F). While this result may be due to differences between the cell types, it is also possible that the primary effect of Nef is to sequester ABCA1 at the plasma membrane and some other HIV protein may cooperate with Nef to stimulate down-regulation of sequestered ABCA1.

The exact molecular mechanisms responsible for the effect of Nef on intracellular trafficking and abundance of ABCA1 are yet to be fully investigated. Nef is known to regulate expression of several transmembrane proteins, including CD4 [45], MHC I [50], MHC II [50], CD28 [51] and DC-SIGN [52]. In most cases, Nef mediates internalization and degradation of the receptor [53], but in some cases (e.g., with DC-SIGN or invariant chain of MHC II) it up-regulates the cell surface expression of the protein. These effects are consistent with our findings showing ABCA1 re-localization and down-regulation, which may involve mechanisms similar to those described for Nef interactions with other proteins. It is worth noting that few of the above-mentioned studies showed co-immunoprecipitation of Nef with a target protein from HIV-infected cells, consistent with our inability to pull down Nef and ABCA1 from HIV-infected macrophages. This may be due to a transitory nature of Nef-ABCA1 interaction and low-level expression of these proteins. Analysis of this interaction in cells overexpressing both proteins demonstrated a critical role of Nef myristoylation (FIG. 5A). This fatty acid may either be directly involved in binding of Nef to ABCA1, similar to the role that farnesylation of yeast pheromone, a-factor, plays in its interaction with the yeast ABC transporter Step 6 [54], or it may regulate Nef-ABCA1 interaction indirectly by targeting Nef to the plasma membrane. Further analysis of the mechanisms by which Nef affects ABCA1 function would require understanding of the molecular events that regulate intracellular trafficking and degradation of ABCA1 in uninfected cells, which is incompletely characterized and is a subject of the ongoing studies.

The results of this study have potential implications for understanding pathogenesis of CAD in HIV-infected patients. These patients have a mildly elevated risk of CAD [55], which is sharply raised by treatment with certain protease inhibitors (PIs) [7,9,14,19]. Increased risk of CAD after treatment with PIs led to the assumption that PIs and/or dyslipidemia are the primary source of development of atherosclerosis in HIV patients. Results presented in this report suggest that HIV-induced impairment of cholesterol efflux from macrophages may be another important contributor to the pathogenesis of CAD. Indeed, inactivation of ABCA1 in macrophages of hyperlipidemic mice significantly increased development of atherosclerosis [27], and genetic mutation inactivating ABCA1 in humans leads to Tangier disease, one of characteristic features of which is an increased risk of CAD [28]. Impairment of reverse cholesterol transport mediated by down-regulation of ABCA1 has been described for bacterial infections and has been linked to pathogenesis of atherosclerosis (reviewed in [56]). In the case of HIV infection, this mechanism would have only a mild atherogenic effect or not at all on the background of hypocholesterolemia characteristic for untreated HIV-1 infection [55,57]. Treatment of HIV-infected patients with HAART causes a sharp rise of triglyceride-rich VLDL, resulting in enhanced lipid uptake and foam cell formation [58], and small dense LDL [59,60], which are particularly susceptible to oxidation [61], are more able to infiltrate the subendothelial space, and are a risk factor for CHD [62]. A combination of these effects of HAART and impairment of cholesterol efflux by HIV (which prevents compensatory removal of excessive cholesterol) would result in a greatly enhanced accumulation of cholesterol in HIV-infected macrophages and would potentially further increase the risk of development of atherosclerosis. It should be noted that HIV-infected macrophages, unlike T cells, survive for extended periods of time and are considered long-term reservoirs of HIV-1 [63]. As a result, infected macrophages persist, at least for some time, in HAART-treated patients, where conditions favor development of atherosclerotic plaques. We can speculate that these macrophages may contribute to initiation of atherosclerotic plaque formation, which then proceeds even in the absence of newly infected cells. This mechanism is consistent with the presence of HIV-infected macrophages in atherosclerotic plaques of HAART-treated patients observed in our study (FIG. 8). However, further in vivo and clinical studies are required to evaluate the contribution of the impairment of reverse cholesterol transport to the risk of atherosclerosis in HIV patients.

Findings presented in this report provide an example of how viruses may interfere with cellular cholesterol metabolism and may potentially affect the risk of atherosclerosis. This example may be not unique to HIV. Other viruses (such as Herpes virus or Cytomegalovirus) were found in atherosclerotic plaques and were epidemiologically associated with elevated risk of development of atherosclerosis [64-66]. Future studies will determine whether these viruses cause disturbances in cholesterol metabolism similar to those found in this study. In support of this possibility, several reports demonstrated that bacterial and viral pathogens may modulate macrophage cholesterol efflux by down-regulating ABC transporters via LXR-dependent [24] and LXR-independent [25] pathways. The first pathway is engaged after activation of Toll-like receptors by invading viruses or bacteria. The second pathway involves the negative effect of bacterial endotoxin on ABCA1 mRNA levels in macrophages [25]. Both pathways promote conversion of macrophages into foam cells, which may acquire resistance to pathogen but retain their atherogenic properties [12]. Therefore, the effect on reverse cholesterol transport may be a common feature of viral and bacterial infection of macrophages, although mechanisms involved are likely unique for each infection.

Results

Impairment of Cholesterol Efflux in HIV-Infected Macrophages

Cholesterol efflux is a pathway for removing excessive cholesterol from cells to extracellular acceptors. It is the first step of reverse cholesterol transport and it plays a key role in maintaining cell cholesterol homeostasis. Impairment of cholesterol efflux leads to accumulation of intracellular cholesterol [26] and development of atherosclerosis in animal models [27] and in humans [28,29]. Analysis of cholesterol efflux from monocyte-derived macrophages infected in vitro with HIV-1 ADA [30] demonstrated a substantial inhibition of apolipoprotein A-I (apoA-I)-specific efflux (FIG. 1A). A similar effect was observed in macrophages infected with two primary macrophage-tropic HIV-1 strains, Yu-2 and 92US660, indicating that impairment of cholesterol efflux is a general feature of HIV-1 replication in macrophages (FIG. 1A). The level of cholesterol efflux inhibition correlated with the level of virus replication (FIG. 1A). Importantly, at the time of analysis (21 days after infection), 80-90% of the cells infected with ADA and Yu-2 viruses were p24-positive (only 20% of the cells infected with 92US660 strain were p24-positive at that time), indicating that RT values in these infections reflected the amount of virus produced per cell and that cholesterol efflux impairment depended on the level of virus protein expression.

Nef is Critical for Cholesterol Efflux Impairment

Previous studies demonstrated that the HIV-1 protein Nef can directly bind cholesterol and suggested that in CD4+ T cells Nef may be involved in transporting cholesterol to the sites of HIV assembly at the plasma membrane [5]. To test the role of Nef in the observed impairment of cholesterol efflux from macrophages, we infected macrophages with HIV-1 SF2 constructs carrying a mutated or a functional Nef gene. To ensure similar levels of infection, the constructs were pseudotyped by the glycoprotein of vesicular stomatitis virus (VSV-G), which targets HIV-1 entry to an endocytic pathway, thus eliminating the requirement for Nef in the early steps of infection [31]. Under these one-cycle replication conditions, both viruses infected about 40% of cells and produced similar levels of p24 (FIG. 1B). Cholesterol efflux to apoA-I was substantially reduced in the culture infected with the Nef-positive virus (WT), whereas in the culture infected with Nef-deficient virus (Nef) it was similar to the level observed in uninfected cells (FIG. 1B). This result indicates that Nef is necessary for HIV-mediated impairment of cholesterol efflux.

To determine whether Nef is sufficient for the observed effect, we transiently transfected murine macrophages RAW 264.7 with constructs expressing SF2-derived Nef (SwissProt accession #P03407) and stimulated ABCA1 expression in these cells by LXR agonist TO-901317. Cholesterol efflux to apoA-I from Nef-transfected RAW 264.7 macrophages was significantly reduced (by more than 50%) compared to cells transfected with an empty vector (mock-transfection) (FIG. 1C). This result indicates that expression of Nef is sufficient to impair cholesterol efflux from macrophages. Interestingly, Nef mutant Nef.G2A, defective in myristoylation and membrane localization [5], was not effective in impairing cholesterol efflux (FIG. 1C) despite levels of expression being similar to that of WT Nef (FIG. 1D). Cholesterol efflux impairment in Nef-transfected RAW cells was less than in HIV-infected macrophages, likely due to differences between these cell types.

Nef Specifically Targets ABCA1-Dependent Cholesterol Efflux

Figure 1:
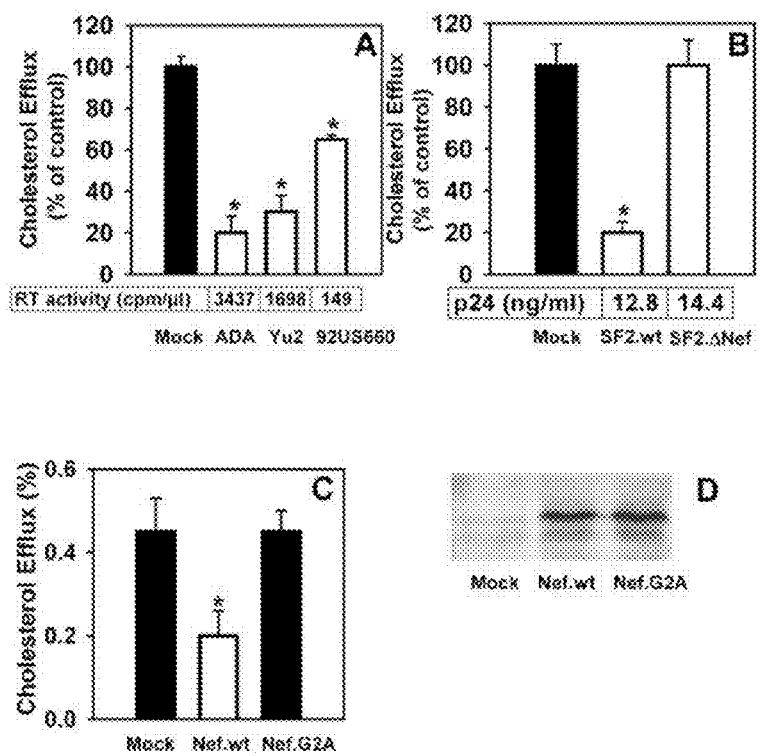
FIG. 1. HIV-1 Nef impairs cholesterol efflux from macrophages.

Specific efflux of cholesterol from cells is mediated by the members of the family of ATP-binding cassette (ABC) transporters. The A1 transporter (ABCA1) is responsible for lipidation of lipid-poor apoA-I with cellular lipids [32], whereas ABCG1 controls efflux to mature HDL [33]. Our finding that Nef inhibits cholesterol efflux to apoA-I (FIG. 1) suggests that ABCA1 may be the specific target of Nef. Consistent with this notion, cholesterol efflux to HDL (controlled by ABCG1) from HIV-infected macrophages was not significantly impaired (FIG. 2A). Furthermore, phospholipid efflux, which is dependent on ABCA1 [34], from Nef-transfected RAW 264.7 macrophages was reduced (FIG. 2B), similar to the effect of Nef on cholesterol efflux (FIG. 1C). In addition, Nef did not affect cholesterol efflux from RAW 264.7 cells where ABCA1 expression was not stimulated (FIG. 2C) and consequently was very low (FIG. 3D).

The notion that ABCA1-mediated efflux is the target of Nef was further supported by experiments in HeLa cells, which do not express ABC transporters and have very low background cholesterol efflux to apoA-I [35]. Consistent with previous report [36], transfection of HeLa cells with ABCA1 (SwissProt accession #O95477) significantly enhanced cholesterol efflux to apoA-I, whereas co-transfection with Nef derived from SF2 or LAI strains (SwissProt accession #P03406) of HIV-1 brought the efflux back to the level observed in mock-transfected cells (FIG. 2D). Importantly, NefLAI, which was expressed to higher levels than NefSF2 (FIG. 2D), was more effective also in cholesterol efflux impairment. A similar experiment testing the effect of Nef on ABCG1-directed cholesterol efflux showed stimulation of cholesterol efflux to HDL after transfection of HeLa cells with ABCG1 (SwissProt accession #P45844) but did not reveal significant inhibition by Nef (FIG. 2E). Therefore, we conclude that Nef specifically targets ABCA1-dependent cholesterol efflux.

Nef Down-Regulates ABCA1

Since ABCA1 appears to be the target of Nef, we tested ABCA1 abundance (by Western blotting) and transcription (by real-time RT-PCR) in HIV-infected human macrophages and Nef-transfected RAW 264.7 cells. Analysis of ABCA1 in macrophages at the peak of HIV-1 ADA replication showed a substantial decrease of ABCA1 abundance (FIG. 3A). Importantly, abundance of two other proteins involved in cholesterol efflux to HDL, ABCG1 and SR-B1, was not affected by HIV infection (FIG. 3A), consistent with specific targeting of the ABCA1-dependent pathway by the virus. A similar phenomenon was observed in Nef-transfected RAW 264.7 macrophages, although the effect was less pronounced (approximately 50% reduction in ABCA1 abundance when assessed by densitometry of the Western blot) (FIG. 3B). The Nef.G2A mutant, which was inactive in cholesterol efflux impairment (FIG. 1C), was also inactive in depleting ABCA1. RT-PCR analysis revealed a significant increase of ABCA1 mRNA in HIV-infected (FIG. 3C) or Nef-transfected (FIG. 3D) cells, which likely reflects a compensatory response for the loss of ABCA1 [37]. This observation rules out an effect of Nef on ABCA1 transcription and suggests a post-transcriptional down-regulation of ABCA1 by Nef. Therefore, down-regulation of ABCA1 is one of the mechanisms responsible for impairment of cholesterol efflux by HIV-1.

Nef Alters Intracellular Distribution of ABCA1

Although down regulation of ABCA1 alone would account for a substantial part of the inhibition of cholesterol efflux, we further found that intracellular distribution of ABCA1 was also affected by HIV infection. Recent reports established that ABCA1 resides both on the plasma membrane and in endocytic vesicles [36], and demonstrated the role of endosomal ABCA1 and trafficking of ABCA1 between endosomes and plasma membrane in the apoA-I-mediated efflux of cellular lipids from the endosomal compartment [38,39]. FIGS. 4A and 4B show p24 staining, and FIGS. 4C and 4D show ABCA1 distribution in human macrophages infected with Nef-deficient (Nef) and Nef-expressing HIV-1 respectively. Consistent with the findings of Neufeld and colleagues [36], ABCA1 was distributed evenly between the cytoplasm and the plasma membrane in human macrophages either uninfected (not shown) or infected with Nef-deficient HIV-1 (Fig 4C), as well as in mock-transfected murine RAW 264.7 cells (FIG. 4E). It appears that in macrophages infected with Nef-expressing HIV-1 ABCA1 was re-localized to the cell periphery (p24-positive cells in FIG. 4D). This re-localization of ABCA1 to the plasma membrane was even more pronounced in Nef-transfected murine macrophages RAW 264.7 (compare FIGS. 4F and 4E). No re-localization of ABCA1 was observed in macrophages transfected with Nef.G2A (FIG. 4G). Therefore, Nef expression induces re-localization of ABCA1, which requires membrane targeting of Nef.

Previous studies demonstrated that apoA-I specifically binds to ABCA1 at the cell surface [40-42]. It was also suggested that trafficking of apoA-I to intracellular cholesterol pools correlates with trafficking of ABCA1 [39,43]. Consistent with re-localization of ABCA1 to the plasma membrane, the specific binding of [$^{125}$I]apoA-I to Nef-transfected RAW 264.7 macrophages was increased (FIG. 4H, left panel). However, internalization of [$^{125}$I]apoA-I was almost completely blocked, supporting the model whereby Nef impairs intracellular trafficking of ABCA1 (FIG. 4H, right panel). Degradation of [$^{125}$I]apoA-I was negligible and was not affected by Nef (not shown).

Therefore, Nef-dependent changes in intracellular distribution of ABCA1 may be another mechanism responsible for impairment of cholesterol efflux.

Nef Interacts with ABCA1

Nef has been shown to modulate expression of several trans-membrane proteins. In some cases (e.g. with CD4 or MHC I) Nef down-regulates the protein, and in some (e.g. with invariant chain of MHC class II or with DC-SIGN) it up-regulates protein's surface expression (ref. [44] and references therein). Some of these effects, including down-regulation of CD4 [45] and MHC I [46], have been shown to depend on an interaction between Nef and the target protein. We therefore tested whether Nef interacts with ABCA1. HeLa cells were co-transfected with Nef or Nef.G2A and FLAG-tagged ABCA1, ABCA1 was immunoprecipitated using anti-FLAG antibody, and immunoprecipitates were analyzed for co-precipitation of Nef. This analysis revealed that Nef co-precipitated with ABCA1, whereas Nef.G2A did not (FIG. 5A, upper panel) despite equally high expression of the two forms of Nef (FIG. 5A lower panel). We conclude that Nef can interact with ABCA1, and this interaction requires myristoylation of Nef and correlates with the ability of Nef to impair cholesterol efflux. The Nef-specific signal observed in this experiment required high level expression of participating proteins, likely due to the transitory nature of Nef interaction with ABCA1.

Interaction between ABCA1 and Nef at the plasma membrane was supported by confocal microscopy, which demonstrated co-localization of Nef and ABCA1 in RAW 264.7 cells transfected with Nef.wt-expressing vector (FIG. 5B). No co-localization was observed between ABCA1 and Nef.G2A (FIG. 5B). This visual analysis was reinforced by an analytical quantification presented in FIG. 5C. Indeed, both ABCA1 and the wild-type Nef proteins are found at the cell periphery and their co-localization is indicated by overlapping green and blue peaks at either end of the graph. Moreover, both colors peak and valley in tandem, suggesting a correlation in subcellular localization of ABCA1 and wild-type Nef. No such correlation is observed in ABCA1 and Nef.G2A distribution. Taken together, these results suggest that interaction between ABCA1 and Nef occurs at the cell plasma membrane.

Therefore, both re-localization and down-modulation of ABCA1 depend on its interaction with Nef, which in turn requires myristoylation and membrane localization of Nef.

HIV-Infected Macrophages Transform into Foam Cells

To determine whether impairment of cholesterol efflux by HIV-1 infection leads to cholesterol accumulation and foam cell formation, we loaded macrophages (uninfected or infected with Nef-expressing or Nef-deficient HIV-1) with lipids by incubating with acetylated LDL (AcLDL) in the presence of apoA-I and stained cellular lipids with Oil Red O. This experiment revealed formation of typical lipid-rich cells in cultures infected with Nef-expressing HIV-1, whereas uninfected cells or macrophages infected with Nef-deficient virus accumulated substantially less cholesterol (compare panels A, B and C in FIG. 6). Analysis by transmission electron microscopy revealed more lipid vacuoles (pointed by arrows in FIG. 6E) in macrophages infected with Nef-expressing HIV-1 than in uninfected cells or cells infected with Nef-deficient HIV-1 (compare FIGS. 6D, 6E and 6F). Cholesterol loading of RAW 264.7 macrophages transfected with Nef also led to accumulation of significantly larger amounts of lipids when compared to cells transfected with an empty vector (compare panels H and I in FIG. 6). In addition, Nef-transfected RAW 264.7 macrophages demonstrated accelerated cholesteryl ester synthesis, especially when cells were loaded with AcLDL (FIG. 6G). Enhanced synthesis of cholesteryl esters is a sensitive indicator of accumulation of cholesterol inside the cells and a key element of foam cell formation.

Measurements of cholesterol mass confirmed substantially higher cholesteryl ester content in Nef-transfected RAW 264.7 macrophages compared to mock-transfected cells (FIG. 7A); there was also more free cholesterol in the transfected macrophages (FIG. 7B). Synthesis of triglycerides was not affected (FIG. 7C) indicating that increased cholesteryl ester synthesis and content is a consequence of increased concentration of cholesterol rather than that of fatty acids. The increased cholesterol content in Nef-transfected cells was not caused by differences in AcLDL uptake, as the latter was similar between Nef-transfected and mock-transfected cells (FIG. 7D). To accommodate the increasing amounts of cholesteryl esters, cells would require an additional amount of phospholipids, and, indeed, the efflux of phospholipids was inhibited (FIG. 2A) while phospholipid synthesis was accelerated in Nef-transfected cells (FIG. 7E). Taken together, these results indicate that HIV-1 infection, via Nef expression, impairs reverse cholesterol transport in macrophages and leads to accumulation of lipids and formation of foam cells.

HIV-Positive Foam Cells in Atherosclerotic Plaques of HIV-Infected Patients

Our finding that HIV-1 infection of macrophages impairs cholesterol efflux from these cells suggests that HIV-infected macrophages may potentially contribute to the development of atherosclerotic plaque, especially when combined with dyslipidemia found in PI-treated patients. Immunostaining of sections of atherosclerotic plaques obtained from HAART-treated HIV-infected patients demonstrated the presence of p24$^+$ macrophages (panels A, B, E and F in FIG. 8). In areas surrounding lipid cores, some p24$^+$ cells displayed a typical foam cell appearance (FIG. 8B). Analysis of parallel consecutive sections stained with anti-CD68 showed that these p24$^+$ cells were located in areas composed of CD68$^+$ cells (FIG. 8C) indicating the macrophage nature of p24+ foam cells. Double immunostaining confirmed this notion by demonstrating the association of p24 staining with CD68$^+$ macrophages and macrophage foam cells (panels E and F). These findings indicate that HIV-infected cholesterol-loaded macrophages are present in the atherosclerotic plaque and therefore may potentially be involved in pathophysiological events leading to the development of atherosclerosis.

Active Cholesterol Efflux Reduces Infectivity of HIV Virions

To determine whether impairment of cholesterol efflux has a role in HIV biology, we compared infectivity of HIV virions produced from monocyte-derived macrophages stimulated or not with an LXR agonist, TO-901317. We hypothesized that if impairment of cholesterol efflux is a specific mechanism to increase HIV replication, then agents counteracting this effect should have anti-HIV activity. LXR agonists up-regulate expression of ABCA1 at a transcriptional level and stimulate cholesterol efflux from various cell types, including human monocyte-derived macrophages ([47] and FIG. 9A). When added to HIV-infected macrophages at day 7 after infection and kept with cells for another 7 days (to allow ABCA1 to accumulate and overcome Nef-mediated inhibition), LXR agonist prevented the impairment of cholesterol efflux by HIV-1 infection (FIG. 9A); in fact, cholesterol efflux from TO-901317-treated HIV-infected macrophages was similar to efflux from uninfected cells stimulated with the LXR agonist. The lack of HIV-specific reduction of cholesterol efflux is likely due to overproduction of ABCA1 which exceeds production of Nef. Virions were collected from TO-901317-treated and untreated cells, adjusted according to p24 content, and analyzed for infectivity using indicator P4-CCR5 cells. This analysis revealed a substantial reduction (by about 80%) of infectivity of virions produced from macrophages treated with LXR agonist (FIG. 9B). Interestingly, protein composition of the virions produced from LXR agonist-treated and untreated cells was very similar (data not shown), whereas virion-associated cholesterol was significantly diminished in virions produced from TO-901317-treated macrophages (FIG. 9C). These results suggest that stimulation of cellular cholesterol efflux may be an effective approach to suppressing HIV replication.

Experimental Procedures

Human monocyte-derived macrophage cultures. Monocyte-derived macrophages were prepared from peripheral blood mononuclear cells of normal donors using adherence to plastic, and differentiated in the presence of macrophage colony-stimulating factor essentially as previously described [67]. No stimulation with LXR agonist was performed unless indicated.

Antibodies. The following antibodies were used for Western blotting: rabbit polyclonal anti-ABCA1 (Novus Biologicals), rabbit polyclonal and mouse monoclonal anti-Nef (AIDS Research and Reference Reagent Program), rabbit polyclonal anti-ABCG1 (Novus Biologicals), rabbit polyclonal anti-SR-B1 (Novus Biologicals), mouse monoclonal anti-B-actin (Sigma).

Viruses and infections. Macrophage-tropic HIV-1 strains Yu-2, and 92US660 were obtained from the NIH AIDS Research and Reference Reagent Program. VSV-G-pseudotyped HIV-1 was prepared by co-transfecting HEK 293T cells with Env-deficient HIV-1 infectious clones [5] and VSV-G-expressing plasmid pHEF-VSVG [68]. All infections were performed using $3.5 \times 10^6$ cpm of RT activity per $10^6$ cells.

FACS analysis of HIV-infected macrophages. To determine the percentage of HIV-infected cells, HIV-infected macrophages were detached from the plate, fixed in 4% formalin/PBS, permeabilized using Becton-Dickinson permeabilization/washing solution (15 min at 4° C.), and incubated with PE-conjugated anti-p24 mAb or isotype control IgG for 30 min at 4° C. After washing, cells were analyzed on a FACScan flow cytometer (Becton Dickinson).

Transfection. RAW 264.7 mouse macrophage cells were transiently transfected using DEAE-dextran method and 5-azacytidine as described previously [69]. The efficiency of transfection was 80-90%. HEK 293T and HeLa cells were transfected using Metafectene reagent (Biontex) following manufacturer's protocol. The efficiency of transfection was 80%.

Cholesterol and phospholipid efflux from RAW264.7 cells. RAW 264.7 cells were incubated in labeling medium containing [$^3$H]cholesterol (75 kBq/ml) or [methyl-$^{14}$C] choline (0.2 MBq/ml) for 48 hours. Cells were then incubated for 18 h in serum-free medium in the presence of the LXR agonist TO-901317 (final concentration 1 M) to stimulate ABCA1 expression and cholesterol efflux. Cells were then washed with PBS and incubated for 3 h in either serum-free medium alone (blank) or in serum-free medium supplemented with 30 μg/ml of lipid-free apoA-I or 30 μg/ml of HDL [70]. For cholesterol efflux analysis, aliquots of medium and cells were counted. Phospholipids were isolated from medium and cells by TLC as described previously [71]. The efflux was calculated as radioactivity in the medium/(radioactivity in the medium+radioactivity remaining in the cells)×100%. ApoA-I-dependent efflux is efflux to apoA-I minus efflux to blank.

Cholesterol efflux from monocyte-derived macrophages and HeLa cells. The same procedure as described above was used except that cells were not stimulated with LXR agonist, and efflux was allowed to proceed for 12 h rather than 3 h used for RAW 264.7 cells. Efflux to serum-free medium supplemented with 30 μg/ml of human serum albumin was used as a control.

Phospholipid biosynthesis. RAW 264.7 cells were incubated in serum-free medium containing [methyl-$^{14}$C] choline (0.2 MBq/ml) for 2 h. Cells were washed, lipids were extracted and separated by TLC [71]. Phospholipid biosynthesis was defined as incorporation of [$^{14}$C]choline into phospholipids per mg of cell protein per 2 h.

Cholesteryl ester and triglyceride biosynthesis and content. RAW 264.7 cells were incubated with or without AcLDL (50 μg/mL) in the presence of 30 ug/ml of lipid-free apoA-I or 5% normolipidemic human plasma for 2 h at 37° C. Cells were then incubated for 2 h with 37 kBq/mL [$^{14}$C]oleic acid (presented to the cells as a BSA-sodium oleate complex). Cells were washed, lipids extracted and [$^{14}$C]oleic acid incorporation into cholesteryl esters and triglyceride was measured after separation of the extracts by TLC [72]. Cellular free and total cholesterol content were measured using enzymatic assay (Roche). Free cholesterol content was calculated as a difference between total and esterified cholesterol.

AcLDL uptake. AcLDL was labeled with $^{125}$I using Iodo-beads (Pierce) according to the manufacturer' instructions, the final specific radioactivity was 100 cpm/ng protein. Cells were incubated with [$^{125}$I]AcLDL at the final concentration 5 ug/ml in the presence or absence of 100-fold excess of unlabeled AcLDL for 2 h at 37° C. The amount of degraded [$^{125}$I]AcLDL in the medium was determined as non-iodine trichloroacetic acid-soluble radioactivity. Cells were then washed and counted and specific AcLDL uptake was calculated as a sum of cell-associated and degraded [$^{125}$I]AcLDL after subtraction of non-specific binding and degradation (i.e. measured in the presence of unlabeled AcLDL).

ApoA-I binding, internalization and degradation. Human apoA-I was labeled with $^{125}$I using Iodobeads; the final specific radioactivity was 200 cpm/ng protein. Cells were incubated with [$^{125}$I]apoA-I at the final concentration 2 μg/ml in the presence or absence of a 100-fold excess of unlabeled apoA-I for 2 h at 37° C. The amount of degraded [$^{125}$I]apoA-I in the medium was determined as non-iodine trichloroacetic acid-soluble radioactivity. Cells were then washed, treated with 0.05% trypsin for 5 min at 37° C. to remove surface-bound [$^{125}$I]apoA-I, and centrifuged. Radioactivity in supernatant (binding) and pellet (internalization) was counted and specific apoA-I binding, internalization and degradation was calculated after subtraction of non-specific values measured in the presence of unlabeled apoA-I.

Co-immunoprecipitation of Nef and ABCA1. HeLa cells were co-transfected with ABCA1-FLAG and Nef. 48 h post transfection, cells were homogenized in PBS and batch immunoprecipitations using M2 affinity gel (Sigma) were carried out according to manufacturer's protocol. Immunoprecipitate was analyzed by Western blotting using polyclonal anti-ABCA1 (Novus Biologicals) and anti-Nef (AIDS Research and Reference Reagent Program) antibodies.

Oil Red O Staining. Human monocyte-derived macrophages and RAW 264.7 cells (stimulated with LXR agonist) were incubated with AcLDL (50 μg/ml) in RPMI 1640 supplemented with 1% Nutridoma (Roche) and 30 μg/ml of lipid-free apoA-I for 18 hrs. After washing with PBS, cells were fixed in 3.7% formaldehyde for 2 min, washed with water, and incubated at room temperature for 1 h with Oil Red O working solution (Fisher Biotech). The Oil Red O solution was removed by aspiration, the cells were washed with water and 0.02% sodium azide was added to the cells. The cells were observed using a reflecting light microscope (90× magnification) fitted with a camera.

Fluorescent Microscopy. For visualization of ABCA1 localization, approximately 106 monocyte-derived macrophages were plated into each well of a 24-well plate containing polylysine coated coverslips (Becton Dickinson Labware) and infected with VSV-G pseudotyped wild-type or Nef-deleted HIV-1 viruses or left uninfected. At 5 days post infection, coverslips with adherent macrophages were removed from the wells, washed with PBS, and cells were fixed with 4% formaldehyde (in PBS) for 20 min at room temperature. After fixing, cells were washed three times with PBS and incubated for 1 h at room temperature in 4% goat serum (in PBS). After washing in PBS, rabbit polyclonal antibody to ABCA1 (Novus Biologicals) and mouse monoclonal antibody to p24 [73] were added in 4% goat serum, 0.1% BSA and 0.1% Saponin. Anti-ABCA1 antibody was added at a 1:500 dilution and anti-p24 antibody—at 1:100. Following a 2 h incubation at room temperature, the coverslips were washed with PBS and incubated with Cy-5-conjugated anti-rabbit and Rhodamine-conjugated anti-mouse secondary antibodies (Jackson Immunoresearch) for 1 h at room temperature. Coverslips were mounted onto slides using Prolong (Molecular Probes) and allowed to dry overnight. Visualization of stained cells was accomplished using a Bio-Rad MRC 1024 confocal laser scanning microscope and software.

RAW 264.7 cells (LXR agonist-stimulated) were grown on collagen-coated cover slips and transfected with Nef-expressing construct or an empty vector. Cells were cultured for 48 h prior to immunostaining, washed with PBS, fixed with 4% formaldehyde and quenched with 50 mM NH$_4$Cl. After permeabilization with 0.5% Triton X-100, cells were incubated with the monoclonal anti-ABCA1 antibody NDF4C2 for 1 h, washed with PBS and incubated in the dark with a secondary goat anti-mouse FITC-labeled antibody for 1 h. For co-localization analysis, monoclonal anti-ABCA1 and polyclonal anti-Nef antibody was used, followed by Cy5-conjugated anti-mouse (staining ABCA1 in blue) and FITC-conjugated anti-rabbit (staining Nef in green) antibodies. Cells were washed again with PBS and after mounting onto glass slides were studied using Zeiss META confocal microscope. Image analysis was performed using the LSM 510 software of the Zeiss microscope which analyzes the distribution of the fluorescence along cell section.

Transmission electron microscopy. Macrophages infected with HIV-1$_{ADA}$ were fixed in 2.5% neutral-buffered glutaraldehyde, pelleted, gelled into agar, post-fixed in 1% OsO$_4$, block-stained in uranyl acetate, dehydrated in graded ethanol and propylene oxide, and embedded in Spurr's resin. Thin sections were stained with uranylacetate and lead citrate and examined on a LEO EM 10 electron microscope at 60 kV.

Real-Time RT-PCR. cDNA was prepared from total cellular RNA from human monocyte-derived macrophages and analyzed by QPCR using IQ Sybr Green Supermix from BIO-RAD (Hecules, C A) according to manufacturer's recommendations with the following primers (300 nM of each primer per sample): ABCA1 sense, 5'-GAGCCTCCCCAG-GAGTCG-3'; ABCA1 antisense, 5'-CAAACATGTCAGCT-GTTACTGGAAG-3'; B-actin sense, 5'-GCCGTACCACTG-GCATCGTG-3'; B-actin antisense, 5'-GTGGTGGTGAAGCTGTA-3'. Primers were ordered from Integration DNA Technologies (Coralville, Iowa). Serial dilutions of ABCA1-pTRE [35] and B-actin cDNA (QPCR Plasmid Standard from Invitrogen) plasmids were used to calculate the copy number of ABCA1 and B-actin cDNA per sample, and results were adjusted according to B-actin cDNA levels. The abundance of ABCA1-specific RNA in RAW cells was determined as described previously [74].

Autopsies. Segments of the aortic wall were removed at autopsy from four HAART-treated AIDS patients (males, aged 39, 40, 44 and 47) at the Institute of Forensic Medicine, Sydney, Australia. The specimens were fixed in formalin and embedded in paraffin. Parallel sections were immunostained with the p24 antibody to detect HIV-1 and anti-CD68 antibody to identify macrophages. Single and double (using DAKO-DOUBLESTAIN™ Kit System 40) immunostaining was carried out as described previously [75]. Sections of lymph nodes excised from the AIDS patients served as a positive control.

Infectivity assay. Virus infectivity was analyzed using P4-CCR5 indicator cells [76] that express B-galactosidase under control of HIV-1 LTR. Briefly, cells were seeded into a 96-well plate at a density of 7,500 cells per well and allowed to adhere overnight. The media was then removed and replaced with virus in suspension (normalized according to RT activity) or with fresh media as a control. Infection was allowed to proceed for 48 hours at 37° C., then the virus was removed, and 100 µl of lysis buffer (B-Galactosidase Enzyme Assay System, Promega) was added. The plate was then frozen overnight at −70° C. to ensure efficient lysis. Upon thawing, 50 ul of lysate was placed into a new 96 well plate, and 50 ul of 2× Assay Buffer was added. The plate was incubated at 37° C. for 1.5 hours and OD readings were taken at 420 nm.

Analysis of virion-associated cholesterol. Seven days post infection with HIV-ADA, [$^3$H]cholesterol was added to the cultures at a final concentration of 75 kBq/ml. 24 hours after addition of cholesterol, the labeled media was removed, the cells were washed with PBS, and the new media was added containing or not 500 nM of LXR agonist, TO-901317 (Sigma). Culture supernatants were collected every 3 days over the period of 2 weeks, pooled, and virions were pelleted by ultracentrifugation, normalized according to p24 value, and the amount of incorporated [$^3$H]cholesterol counted on a beta-counter.

Statistical analysis. All experiments were reproduced two to four times, and representative experiments are shown. Student's t test was used to determine statistical significance of the differences.

Exemplary Methods

As exemplified above, the present invention is identifying Nef as a causative factor for impairment of cholesterol efflux in HIV-1 infected cells. Impairment of cholesterol efflux relates to CAD and HIV infection. This utility provides methods, generally described below, for (i) treating coronary artery disease in HIV-1-infected individuals; (ii) for suppressing HIV infection; and (iii) methods for monitoring therapeutic treatments designed to effectively treat such disease.

(i) Treatment of Coronary Artery Disease in HIV-1-Infected Individuals

The methods for treating coronary artery disease in HIV-1-infected cells under the invention comprise:
  (1) intracellular administering an effective amount of Nef-neutralizing antibody or a fragment thereof sufficient to inhibit the binding of Nef binding to ABCA1, wherein the antibody is a human polyclonal antibody, monoclonal antibody or a chimeric antibody; or
  (2) intracellular administering an effective amount of Nef-targeting small molecules sufficient to inhibit the binding of Nef binding to ABCA1.
  (3) Intracellular administering an effective amount of chemical agents sufficient to stimulate expression of ABCA1 and cholesterol efflux in HIV-1-infected cells. Examples of the chemical agents include, but are not limited to, agonists of LXR, RXR, or PPAR nuclear receptors.

(ii) Suppression of HIV Infection

The methods for suppressing HIV infection under the invention comprise stimulating cholesterol efflux from cells by stimulating expression of ABCA1 using chemical agents. Examples of the chemical agents include, but are not limited to, agonists of LXR, RXR or PPAR nuclear receptors.

Equivalents

It is well understood that various other modifications will be apparent to, and can readily be made by those skilled in the art without departing from the scope and spirit of this invention. Accordingly, it is not intended that the scope of the invention be limited to the description set forth above, but rather be construed as encompassing all of the features of patentable novelty which reside in the present invention, including all features which would be treated as equivalents thereof by those skilled in the art to which the invention pertains.

Incorporation by Reference

Appended below, as a part of the invention disclosure, is a list of references which recites seventy-six (76) publications considered relevant and which are incorporated herein in their entirety as they may be necessary to establish and/or provide to a person or ordinary skill in the art information to make and use the claimed invention.

References

1. Maziere J C, Landureau J C, Giral P, Auclair M, Fall L, Lachgar A, Achour A, Zagury D (1994) Lovastatin inhibits HIV-1 expression in H9 human T lymphocytes cultured in cholesterol-poor medium. Biomed Pharmacother 48: 63-67.
2. Ono A, Freed E O (2001) Plasma membrane rafts play a critical role in HIV-1 assembly and release. Proc Natl Acad Sci USA 98: 13925-13930.
3. Campbell S M, Crowe S M, Mak J (2002) Virion-associated cholesterol is critical for the maintenance of HIV-1 structure and infectivity. Aids 16: 2253-2261.
4. Guyader M, Kiyokawa E, Abrami L, Turelli P, Trono D (2002) Role for human immunodeficiency virus type 1 membrane cholesterol in viral internalization. J Virol 76: 10356-10364.
5. Zheng Y H, Plemenitas A, Fielding C J, Peterlin B M (2003) Nef increases the synthesis of and transports cholesterol to lipid rafts and HIV-1 progeny virions. Proc Natl Acad Sci USA 100: 8460-8465.
6. Barbara G (2002) Cardiovascular manifestations of HIV infection. Circulation 106: 1420-1425.
7. El-Sadr W. M., Mullin C. M., Carr A., Gibert C, Rappoport C, Visnegarwala F., Grunfeld C, Raghavan S. S. (2005) Effects of HIV disease on lipid, glucose and insulin levels: results from a large antiretroviral-naive cohort. HIV Med 6: 114-121.
8. Escaut L, Monsuez J J, Chironi G, Merad M, Teicher E, Smadja D, Simon A, Vittecoq D (2003) Coronary artery disease in HIV infected patients. Intensive Care Med 29: 969-973.
9. Hsue P Y, Lo J C, Franklin A, Bolger A F, Martin J N, Deeks S G, Waters D D (2004) Progression of atherosclerosis as assessed by carotid intima-media thickness in patients with HIV infection. Circulation 109: 1603-1608.
10. Blum A, Hadas V, Burke M, Yust I, Kessler A (2005) Viral load of the human immunodeficiency virus could be an independent risk factor for endothelial dysfunction. Clin Cardiol 28: 149-153.

11. Lusis A J (2000) Atherosclerosis. Nature 407: 233-241.
12. Blessing E, Kuo Cc, Lin T M, Campbell L A, Bea F, Chesebro B, Rosenfeld M E (2002) Foam Cell Formation Inhibits Growth of *Chlamydia pneumoniae* but Does Not Attenuate *Chlamydia pneumoniae*-Induced Secretion of Proinflammatory Cytokines. Circulation 105: 1976-1982.
13. Grunfeld C, Pang M, Doerrler W, Shigenaga J K, Jensen P, Feingold K R (1992) Lipids, lipoproteins, triglyceride clearance, and cytokines in human immunodeficiency virus infection and the acquired immunodeficiency syndrome. J Clin Endocrinol Metab 74: 1045-1052.
14. Crook M A, Mir N (1999) Abnormal lipids and the acquired immunodeficiency syndrome: is there a problem and what should we do about it? Int J STD AIDS10: 353-356.
15. Liang J S, Distler O, Cooper D A, Jamil H, Deckelbaum R J, Ginsberg H N, Sturley S L (2001) HIV protease inhibitors protect apolipoprotein B from degradation by the proteasome: a potential mechanism for protease inhibitor-induced hyperlipidemia. Nat Med 7: 1327-1331.
16. Nguyen A T, Gagnon A, Angel J B, Sorisky A (2000) Ritonavir increases the level of active ADD-1/SREBP-1 protein during adipogenesis. AIDS 14: 2467-2473.
17. Dressman J, Kincer J, Matveev S V, Guo L, Greenberg R N, Guerin T, Meade D, Li X A, Zhu W, Uittenbogaard A, Wilson M E, Smart E J (2003) HIV protease inhibitors promote atherosclerotic lesion formation independent of dyslipidemia by increasing CD36-dependent cholesteryl ester accumulation in macrophages. J Clin Invest 111: 389-397.
18. Klein D, Hurley L B, Quesenberry C P, Jr., Sidney S (2002) Do protease inhibitors increase the risk for coronary heart disease in patients with HIV-1 infection? J Acquir Immune Defic Syndr 30: 471-477.
19. Charakida M, Donald A E, Green H, Storry C, Clapson M, Caslake M, Dunn D T, Halcox J P, Gibb D M, Klein N J, Deanfield J E (2005) Early structural and functional changes of the vasculature in HIV-infected children: impact of disease and antiretroviral therapy. Circulation 112: 103-109.
20. David M H, Hornung R, Fichtenbaum C J (2002) Ischemic cardiovascular disease in persons with human immunodeficiency virus infection. Clin Infect Dis 34: 98-102.
21. Neumann T, Woiwoid T, Neumann A, Miller M, Ross B, Volbracht L, Brockmeyer N, Gerken G, Erbel R (2003) Cardiovascular risk factors and probability for cardiovascular events in HIV-infected patients: part I. Differences due to the acquisition of HIV-infection. Eur J Med Res 8: 229-235.
22. Varriale P, Saravi G, Hernandez E, Carbon F (2004) Acute myocardial infarction in patients infected with human immunodeficiency virus. Am Heart J 147: 55-59.
23. Jessup W, Gelissen I C, Gaus K, Kritharides L (2006) Roles of ATP binding cassette transporters A1 and G1, scavenger receptor BI and membrane lipid domains in cholesterol export from macrophages. Curr Opin Lipidol 17: 247-257.
24. Castrillo A, Joseph S B, Vaidya S A, Haberland M, Fogelman A M, Cheng G, Tontonoz P (2003) Crosstalk between LXR and toll-like receptor signaling mediates bacterial and viral antagonism of cholesterol metabolism. Mol Cell 12: 805-816.
25. Khovidhunkit W, Moser A H, Shigenaga J K, Grunfeld C, Feingold K R (2003) Endotoxin down-regulates ABCG5 and ABCG8 in mouse liver and ABCA1 and ABCG1 in J774 murine macrophages: differential role of LXR. Journal of Lipid Research 44: 1728-1736.
26. Feng B, Tabas I (2002) ABCA1-mediated cholesterol efflux is defective in free cholesterol-loaded macrophages. Mechanism involves enhanced ABCA1 degradation in a process requiring full NPC1 activity. J Biol Chem 277: 43271-43280.
27. Aiello R J, Brees D, Bourassa P A, Royer L, Lindsey S, Coskran T, Haghpassand M, Francone O L (2002) Increased atherosclerosis in hyperlipidemic mice with inactivation of ABCA1 in macrophages. Arterioscler Thromb Vase Biol 22: 630-637.
28. Oram J F (2000) Tangier disease and ABCA1. Biochim Biophys Acta 1529: 321-330.
29. Attie A D, Kastelein J P, Hayden M R (2001) Pivotal role of ABCA1 in reverse cholesterol transport influencing HDL levels and susceptibility to atherosclerosis. J Lipid Res 42: 1717-1726.
30. Gendelman H E, Orenstein J M, Martin M A, Ferrua C, Mitra R, Phipps T, Wahl L A, Lane H C, Fauci A S, Burke D S (1988) Efficient isolation and propagation of human immunodeficiency virus on recombinant colony-stimulating factor 1-treated monocytes. J Exp Med 167: 1428-1441.
31. Aiken C (1997) Pseudotyping human immunodeficiency virus type 1 (HIV-1) by the glycoprotein of vesicular stomatitis virus targets HIV-1 entry to an endocytic pathway and suppresses both the requirement for Nef and the sensitivity to cyclosporin A. J Virol 71: 5871-5877.
32. Oram J F, Lawn R M (2001) ABCA1. The gatekeeper for eliminating excess tissue cholesterol. J Lipid Res 42: 1173-1179.
33. Kennedy M A, Barrera G C, Nakamura K, Baldan A, Tarr P, Fishbein M C, Frank J, Francone O L, Edwards P A (2005) ABCG1 has a critical role in mediating cholesterol efflux to HDL and preventing cellular lipid accumulation. Cell Metab 1: 121-131.
34. Oram J F (2003) HDL apolipoproteins and ABCA1: partners in the removal of excess cellular cholesterol. Arterioscler Thromb Vase Biol 23: 720-727.
35. Remaley A T, Stonik J A, Demosky S J, Neufeld E B, Bocharov A V, Vishnyakova T G, Eggerman T L, Patterson A P, Duverger N J, Santamarina-Fojo S, Brewer H B, Jr. (2001) Apolipoprotein specificity for lipid efflux by the human ABCAI transporter. Biochem Biophys Res Commun 280: 818-823.
36. Neufeld E B, Remaley A T, Demosky S J, Stonik J A, Cooney A M, Comly M, Dwyer N K, Zhang M, Blanchette-Mackie J, Santamarina-Fojo S, Brewer H B, Jr. (2001) Cellular Localization and Trafficking of the Human ABCA1 Transporter. J Biol Chem 276: 27584-27590.
37. Albrecht C, Soumian S, Amey J S, Sardini A, Higgins C F, Davies A H, Gibbs R G (2004) ABCA1 expression in carotid atherosclerotic plaques. Stroke 35: 2801-2806.
38. Neufeld E B, Stonik J A, Demosky S J, Jr., Knapper C L, Combs C A, Cooney A, Comly M, Dwyer N, Blanchette-Mackie J, Remaley A T, Santamarina-Fojo S, Brewer H B, Jr. (2004) The ABCA1 transporter modulates late endocytic trafficking: insights from the correction of the genetic defect in Tangier disease. J Biol Chem 279: 15571-15578.

39. Chen W, Wang N, Tall A R (2005) A PEST deletion mutant of ABCA1 shows impaired internalization and defective cholesterol efflux from late endosomes. J Biol Chem 280: 29277-29281.
40. Wang N, Silver D L, Costet P, Tall A R (2000) Specific binding of ApoA-I, enhanced cholesterol efflux, and altered plasma membrane morphology in cells expressing ABC1. J Biol Chem 275: 33053-33058.
41. Oram J F, Lawn R M, Garvin M R, Wade D P (2000) ABCA1 Is the cAMP-inducible Apolipoprotein Receptor That Mediates Cholesterol Secretion from Macrophages. J Biol Chem 275: 34508-34511.
42. Denis M, Haidar B, Marcil M, Bouvier M, Krimbou L, Genest J, Jr. (2004) Molecular and cellular physiology of apolipoprotein A-I lipidation by the ATP-binding cassette transporter A1 (ABCA1). J Biol Chem 279: 7384-7394.
43. Le Goff W, Peng D Q, Settle M, Brubaker G, Morton R E, Smith J D (2004) Cyclosporin A traps ABCA1 at the plasma membrane and inhibits ABCA1-mediated lipid efflux to apolipoprotein A-I. Arterioscler Thromb Vase Biol 24: 2155-2161.
44. Coleman S H, Madrid R, Van Damme N, Mitchell R S, Bouchet J, Servant C, Pillai S, Benichou S, Guatelli J C (2006) Modulation of cellular protein trafficking by human immunodeficiency virus type 1 Nef: role of the acidic residue in the ExxxLL motif. J Virol 80: 1837-1849.
45. Garcia J V, Miller A D (1991) Serine phosphorylation-independent downregulation of cell-surface CD4 by nef. Nature 350: 508-511.
46. Kasper M R, Roeth J F, Williams M, Filzen T M, Fleis R I, Collins K L (2005) HIV-1 Nef disrupts antigen presentation early in the secretory pathway. J Biol Chem 280: 12840-12848.
47. Sparrow C P, Baffic J, Lam M H, Lund E G, Adams A D, Fu X, Hayes N, Jones A B, Macnaul K L, Ondeyka J, Singh S, Wang J, Zhou G, Moller D E, Wright S D, Menke J G (2002) A potent synthetic LXR agonist is more effective than cholesterol loading at inducing ABCA1 mRNA and stimulating cholesterol efflux. J Biol Chem 277: 10021-10027.
48. Liao Z, Cimakasky L M, Hampton R, Nguyen D H, Hildreth J E (2001) Lipid rafts and HIV pathogenesis: host membrane cholesterol is required for infection by HIV type 1. AIDS Res Hum Retroviruses 17: 1009-1019.
49. Chen W, Sun Y, Welch C, Gorelik A, Leventhal A R, Tabas I, Tall A R (2001) Preferential ATP-binding cassette transporter A1-mediated cholesterol efflux from late endosomes/lysosomes. J Biol Chem 276: 43564-43569.
50. Schwartz O, Marechal V, Le Gall S, Lemonnier F, Heard J M (1996) Endocytosis of major histocompatibility complex class I molecules is induced by the HIV-1 Nef protein. Nat Med 2: 338-342.
51. Swigut T, Shohdy N, Skowronski J (2001) Mechanism for down-regulation of CD28 by Nef. EMBO J 20: 1593-1604.
52. Sol-Foulon N, Moris A, Nobile C, Boccaccio C, Engering A, Abastado J P, Heard J M, van Kooyk Y, Schwartz O (2002) HIV-1 Nef-induced upregulation of DC-SIGN in dendritic cells promotes lymphocyte clustering and viral spread. Immunity 16: 145-155.
53. Arora V K, Fredericksen B L, Garcia J V (2002) Nef: agent of cell subversion. Microbes Infect 4: 189-199.
54. Caldwell G A, Wang S H, Naider F, Becker J M (1994) Consequences of altered isoprenylation targets on a-factor export and bioactivity. Proc Natl Acad Sci USA 91: 1275-1279.
55. Riddler S A, Smit E, Cole S R, Li R, Chmiel J S, Dobs A, Palella F, Visscher B, Evans R, Kingsley L A (2003) Impact of HIV Infection and HAART on Serum Lipids in Men. JAMA 289: 2978-82.
56. Khovidhunkit W, Kim M S, Memon R A, Shigenaga J K, Moser A H, Feingold K R, Grunfeld C (2004) Thematic review series: The Pathogenesis of Atherosclerosis. Effects of infection and inflammation on lipid and lipoprotein metabolism mechanisms and consequences to the host. J Lipid Res 45: 1169-1196.
57. Shor-Posner G, Basit A, Lu Y, Cabrejos C, Chang J, Fletcher M, Mantero-Atienza E, Baum MK (1993) Hypocholesterolemia is associated with immune dysfunction in early human immunodeficiency virus-1 infection. Am J Med 94: 515-519.
58. Gianturco S H, Ramprasad M P, Song R, Li R, Brown M L, Bradley W A (1998) Apolipoprotein B-48 or its apolipoprotein B-100 equivalent mediates the binding of triglyceride-rich lipoproteins to their unique human monocyte-macrophage receptor. Arterioscler Thromb Vase Biol 18: 968-976.
59. Stein J H, Klein M A, Bellehumeur J L, McBride P E, Wiebe D A, Otvos J D, Sosman J M (2001) Use of human immunodeficiency virus-1 protease inhibitors is associated with atherogenic lipoprotein changes and endothelial dysfunction. Circulation 104: 257-262.
60. Badiou S, Merle D B, Dupuy A M, Baillat V, Cristol J P, Reynes J (2003) Decrease in LDL size in HIV-positive adults before and after lopinavir/ritonavir-containing regimen: an index of atherogenicity? Atherosclerosis 168: 107-113.
61. Chait A, Brazg R L, Tribble D L, Krauss R M (1993) Susceptibility of small, dense, low-density lipoproteins to oxidative modification in subjects with the atherogenic lipoprotein phenotype, pattern B. Am J Med 94: 350-356.
62. St Pierre A C, Ruel I L, Cantin B, Dagenais G R, Bernard P M, Despres J P, Lamarche B (2001) Comparison of various electrophoretic characteristics of LDL particles and their relationship to the risk of ischemic heart disease. Circulation 104: 2295-2299.
63. Aquaro S, Bagnarelli P, Guenci T, De Luca A, Clementi M, Balestra E, Calio R, Perno C F (2002) Long-term survival and virus production in human primary macrophages infected by human immunodeficiency virus. J Med Virol 68: 479-488.
64. Leinonen M, Saikku P (2002) Evidence for infectious agents in cardiovascular disease and atherosclerosis. Lancet Infect Dis 2: 11-17.
65. Morre S A, Stooker W, Lagrand W K, van den Brule A J, Niessen H W (2000) Microorganisms in the aetiology of atherosclerosis. J Clin Pathol 53: 647-654.
66. Streblow D N, Orloff S L, Nelson J A (2001) Do pathogens accelerate atherosclerosis? J Nutr 131: 2798S-2804S.
67. Schmidtmayerova H, Nuovo G J, Bukrinsky M (1997) Cell proliferation is not required for productive HIV-1 infection of macrophages. Virology 232: 379-84.
68. Chang L J, Urlacher V, Iwakuma T, Cui Y, Zucali J (1999) Efficacy and safety analyses of a recombinant human immunodeficiency virus type 1 derived vector system. Gene Ther 6: 715-728.

69. Escher G, Hoang A, Georges S, Tchoua U, El Osta A, Krozowski Z, Sviridov D (2005) Demethylation using the epigenetic modifier, 5-azacytidine, increases the efficiency of transient transfection of macrophages. J Lipid Res 46: 356-365.
70. Sviridov D, Pyle L E, Fidge N (1996) Efflux of cellular cholesterol and phospholipid to apolipoprotein A-I mutants. J Biol Chem 271: 33277-33283.
71. Sviridov D, Hoang A, Huang W, Sasaki J (2002) Structure-function studies of apoA-I variants: site-directed mutagenesis and natural mutations. J Lipid Res 43: 1283-1292.
72. Fu Y, Hoang A, Escher G, Parton R G, Krozowski Z, Sviridov D (2004) Expression of Caveolin-1 Enhances Cholesterol Efflux in Hepatic Cells. J Biol Chem 279: 14140-14146.
73. Simm M, Shahabuddin M, Chao W, Allan J S, Volsky D J (1995) Aberrant Gag protein composition of a human immunodeficiency virus type 1 vif mutant produced in primary lymphocytes. J Virol 69: 4582-4586.
74. Fu Y, Hoang A, Escher G, Parton R G, Krozowski Z, Sviridov D (2004) Expression of Caveolin-1 Enhances Cholesterol Efflux in Hepatic Cells. J Biol Chem 279: 14140-14146.
75. Bobryshev Y V, Lord R S (1998) Mapping of vascular dendritic cells in atherosclerotic arteries suggests their involvement in local immune-inflammatory reactions. Cardiovasc Res 37: 799-810.
76. Charneau P, Mirambeau G, Roux P, Paulous S, Buc H, Clavel F (1994) HIV-1 reverse transcription. A termination step at the center of the genome. J Mol Biol 241: 651-662.

The invention claimed is:

1. A method of suppressing HIV replication in an individual infected with human immunodeficiency virus (HIV) comprising administering to the individual an effective amount of a Liver X receptor (LXR) agonist comprising TO-901317, wherein the LXR agonist prevents cholesterol delivery and incorporation into HIV by stimulation of expression of ATP binding cassette transporter A1 (ABCA1).

2. The method of claim 1, wherein the stimulation of expression of ABCA1 reduces HIV control of cholesterol trafficking in infected cells and stimulates efflux of cholesterol from the infected cells to extracellular molecules.

3. The method of claim 2, wherein the extracellular molecule comprises apo A-1 or a fragment thereof.

4. The method of claim 3 wherein apo A-1 comprises a Nef targeting molecule.

5. The method of claim 1, wherein the HIV comprises HIV-1.

* * * * *